(12) United States Patent
Yamamoto et al.

(10) Patent No.: US 7,067,668 B2
(45) Date of Patent: Jun. 27, 2006

(54) 4-QUINOLINOL DERIVATIVES AND FUNGICIDES CONTAINING THE SAME AS AN ACTIVE INGREDIENT USED FOR AGRICULTURE AND HORTICULTURE

(75) Inventors: Kazumi Yamamoto, Yokohama (JP); Takeshi Teraoka, Yokohama (JP); Michiaki Iwata, Yokohama (JP); Keiichi Imamura, Yokohama (JP); Hiroshi Kurihara, Yokohama (JP); Norio Sasaki, Ibaraki (JP); Yoshihiro Usui, Ryugasaki (JP); Nobumitsu Sawai, Chiba (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 172 days.

(21) Appl. No.: 10/715,846

(22) Filed: Nov. 19, 2003

(65) Prior Publication Data

US 2004/0152728 A1     Aug. 5, 2004

Related U.S. Application Data

(63) Continuation of application No. 09/424,257, filed as application No. PCT/JP98/02434 on Jun. 2, 1998, now Pat. No. 6,680,282.

(30) Foreign Application Priority Data

Jun. 2, 1997    (JP) ................................ 9-144266

(51) Int. Cl.
   *C07D 215/16*     (2006.01)
   *C07D 221/22*     (2006.01)
(52) U.S. Cl. ................... 546/153; 546/79; 546/103
(58) Field of Classification Search ............... 546/153, 546/79, 103
   See application file for complete search history.

(56) References Cited

U.S. PATENT DOCUMENTS

| 3,636,216 | A | | 1/1972 | Baron |
| 4,168,311 | A | | 9/1979 | Studeneer |
| 5,190,952 | A | | 3/1993 | Minowa et al. |
| 5,194,617 | A | | 3/1993 | Minowa |
| 5,391,553 | A | | 2/1995 | Shutske |
| 5,994,368 | A | * | 11/1999 | Oku et al. ................ 514/312 |
| 6,680,282 | B1 | * | 1/2004 | Yamamoto et al. ......... 504/247 |

FOREIGN PATENT DOCUMENTS

| DE | 23 61 438 A | 6/1975 |
| EP | 0 326 328 | 8/1989 |
| EP | 0 326 330 | 8/1989 |
| EP | 0 326 331 | 8/1989 |
| EP | 0 374 765 A | 6/1990 |
| EP | 0 407 192 | 1/1991 |
| EP | 0 669 320 | 8/1995 |
| JP | 41020094 | 11/1963 |
| JP | 1-246263 | 10/1989 |
| JP | 1-246264 | 10/1989 |
| JP | 1-246266 | 10/1989 |
| JP | 3-128355 | 5/1991 |
| JP | 5-202032 | 8/1993 |
| JP | 5-271222 | 10/1993 |
| JP | 7-285938 | 10/1995 |
| JP | 09 309879 A | 12/1997 |
| JP | 09309879 | 12/1997 |
| WO | 9636608 | 11/1996 |

OTHER PUBLICATIONS

C.C. Price, et al., Organic Synthesis Collective, vol. 3, pp. 272-275, "4,7-DICHLOROQUINOLINE," 1995.
C.R. Hauser, et al., Journal of American Chemical Society, vol. 70, pp. 2402-2404, "Reactions of β-Keto Esters With Aromatic Amines. Synthesis of 2- and 4-Hydroxyquinoline Derivatives," 1998.
N. Minowa, et al., Biosci. Biotech. Biochem., vol. 60, N. 9, pp. 1510-1512, "New Insecticidal 4-Acetoxy-2-Alkenyl-quinolines," 1996.
N. Minowa, et a., Biosci. Biotech. Biochem., vol. 61, No. 7, pp. 1213-1215, "Synthesis and Insecticidal Activity of New 2- and 6-Substituted 4-Acetoxyquinolines," 1997.
Ebeid My et al. Egypt. J. Pharm. Sci. (1991), 32(3-4), 653-62.
Chung KH et al. Han'guk Nonghwa Hahoechi (1991), 34(1), 43-8.
Nasr M and Burckhalter JH. J. Heterocycl. Chem. (1979), 16(3), 497-500.
Chudgar RJ and Trivedi KN. J. Indian Chem. Soc. (1972), 49(5), 513-18.
Gyul'budagyan LV et a. Khim. Geterotsikl. Soedin. (1970), (7), 966-8.
Gyul'budagyan LV et al. Uch. Zap., Erevan. gos. Univ. (1967), No. 2, 65-71.
Chung et al. Han'guk Nonghwa Hakhoechi (1990), 33(30), 264-7.
J. Indian Chem. Soc. (JICSAH, 00194522); 1982; vol. 59 (3); pp. 367-369 (English Abstract Only).
Chudgar RJ et al. J. Indian Chem. Soc. (1972), 49 (5), 513-18.

* cited by examiner

*Primary Examiner*—D. Margaret Seaman
(74) *Attorney, Agent, or Firm*—Oblon, Spivak, McClelland, Maier & Neustadt, P.C.

(57)  ABSTRACT

A new agricultural and horticultural fungicide having an excellent control effect is provided.

4-Quinolinol derivatives represented by the following formula:

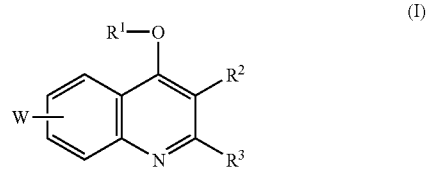

(I)

or agriculturally and horticulturally acceptable acid addition salts thereof.

30 Claims, No Drawings

4-QUINOLINOL DERIVATIVES AND FUNGICIDES CONTAINING THE SAME AS AN ACTIVE INGREDIENT USED FOR AGRICULTURE AND HORTICULTURE

This application is a continuation of U.S. application Ser. No. 09/424,257 filed on Mar. 21, 2000 now U.S. Pat. No. 6,680,282, now allowed, which is a 371 of PCT/JP98/02434, filed Jun. 2, 1998.

FIELD OF THE INVENTION

The present invention relates to 4-quinolinol derivatives and agricultural and horticultural fungicides containing them as active ingredients.

BACKGROUND OF THE INVENTION

JP-01246263A, JP-05202032A, JP-05271222A and JP-07285.938A, which were published prior to the filing date of the present application, disclose that quinoline derivatives having a substituent, such as aryloxy, arylthio, amino, pyrimidyloxy, pyrimidylthio or benzoyl group, at 4-position of quinoline skeleton are effective against plant pathogenic fungi and useful as agricultural and horticultural fungicides. However, it has never known that a quinoline derivative having an acyloxy group at 4-position of quinoline skeleton has an excellent fungicidal activity.

And, JP-03128355A discloses 4-acyloxyquinoline derivatives structurally similar to the compound of the present invention and insecticidal and acaricidal agents containing them as active ingredients. However, it has never known that these compounds are effective against plant pathogenic fungi.

DISCLOSURE OF THE INVENTION

Many active agents having control effect against various plant diseases were discovered and various agricultural and horticultural fungicides containing them as active ingredients have been developed. Due to some problems, such as an appearance of resistant fungi, however, fungicides having higher control effect are needed.

Thus, an object of the present invention is to provide a new agricultural and horticultural fungicide having higher control effect.

The present inventors concentrated on solving the above-mentioned problem. As the result, it was found that among 4-quinolinol derivatives, 4-quinolinol derivatives having specific substituents at all of the 2, 3 and 5 to 8 positions of quinoline skeleton and their acid addition salts show excellent fungicidal activity against various plant pathogenic fungi causing blast of rice, brown spot of rice, powdery mildew of *Cucurbitaceae,* anthracnose of potato and the like, and thereby the present invention was completed.

Accordingly, the present invention relates to a 4-quinolinol derivative represented by the general formula (I):

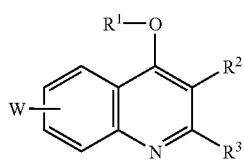

(I)

wherein
$R^1$ represents
  a hydrogen atom,
  an alkali metal,
  an alkaline earth metal, or
  $COR^4$ in which $R^4$ is
    a hydrogen atom,
    an optionally substituted $C_1$–$C_{18}$ alkyl group,
    an optionally substituted $C_2$–$C_{18}$ alkenyl group,
    an optionally substituted $C_3$–$C_{10}$ cycloalkyl group,
    an optionally substituted phenyl lower alkyl group,
    an optionally substituted phenoxy lower alkyl group,
    an optionally substituted aryl group,
    $OR^5$ in which $R^5$ is an optionally substituted lower alkyl group, an optionally substituted aryl group, an optionally substituted heterocycle, an optionally substituted phenyl lower alkyl group or an optionally substituted phenoxy lower alkyl group, or
    $NR^6R^7$ in which $R^6$ and $R^7$ are each a hydrogen atom, an optionally substituted $C_1$–$C_6$ alkyl group or an optionally substituted phenyl group, or $R^6$ and $R^7$ together with N may form a four- to six-membered ring containing one or two heteroatoms;
$R^2$ represents an optionally substituted lower alkyl group;
$R^3$ represents
  an optionally substituted $C_{11}$–$C_{18}$ alkyl group,
  an optionally substituted lower alkenyl group, or
  an optionally substituted lower alkoxy group; or
$R^2$ and $R^{13}$ together represent —$(CH_2)_m$— in which m is 3 or 4; and
W represents 1 to 4 substituents on the nucleus which may be identical or different and each of which is
  a halogen atom,
  an optionally substituted $C_1$–$C_{10}$ alkyl group,
  an optionally substituted lower alkenyl group,
  an optionally substituted lower alkynyl group,
  an optionally substituted $C_1$–$C_{10}$ alkoxy group,
  an optionally substituted $C_3$–$C_{10}$ cycloalkyl group,
  an optionally substituted aryl group,
  an optionally substituted aryloxy group,
  $NR^8R^9$ in which $R^8$ and $R^9$ are each a hydrogen atom, an optionally substituted $C_1$–$C_6$ alkyl group or an optionally substituted phenyl group, or $R^8$ and $R^9$ together with N may form a four- to six-membered ring containing one or two heteroatoms,
  $COR^{10}$ in which $R^{10}$ is a hydrogen atom, an optionally substituted lower alkyl group or an optionally substituted lower alkenyl group,
  $COOR^{11}$ in which $R^{11}$ is a hydrogen atom, an optionally substituted lower alkyl group or an optionally substituted lower alkenyl group,
  a nitro group or
  a cyano group, and acid addition salts thereof as well as an agricultural and horticultural fungicide containing at least one of them.

In the 4-quinolinol derivatives represented by the aforementioned general formula (I),
$R^1$ represents
  a hydrogen atom,
  an alkali metal, such as preferably sodium and potassium,
  an alkaline earth metal, such as magnesium, calcium and barium, in which magnesium and calcium are preferable, or COR$^4$ in which R$^4$ is
- a hydrogen atom,
- an optionally substituted C$_1$–C$_{18}$ alkyl group, preferably an optionally substituted C$_1$–C$_8$ alkyl group, more preferably a C$_1$–C$_4$ alkyl group, such as methyl, ethyl, propyl, isopropyl, butyl, isobutyl and t-butyl,
- an optionally substituted C$_2$–C$_{18}$ alkenyl group, preferably an optionally substituted C$_2$–C$_8$ alkenyl group, more preferably a C$_2$–C$_4$ alkenyl group, such as vinyl group CH$_2$=CH—, allyl group CH$_2$=CHCH$_2$— and 2-butenyl group CH$_3$CH=CHCH$_2$—,
- an optionally substituted C$_3$–C$_{10}$ cycloalkyl group, preferably an optionally substituted C$_3$–C$_6$ cycloalkyl group,
- an optionally substituted phenyl lower alkyl group,
- an optionally substituted phenoxy lower alkyl group,
- an optionally substituted aryl group,
- OR$^5$ in which R$^5$ is an optionally substituted lower alkyl group, an optionally substituted aryl group, an optionally substituted heterocycle, an optionally substituted phenyl lower alkyl group or an optionally substituted phenoxy lower alkyl group, or
- NR$^6$R$^7$ in which R$^6$ and R$^7$ are each a hydrogen atom, an optionally substituted C$_1$–C$_6$ alkyl group or an optionally substituted phenyl group, or R$^6$ and R$^7$ together with N may form a four- to six-membered ring containing one or two heteroatoms;

R$^2$ represents an optionally substituted C$_1$–C$_4$ alkyl group;
R$^3$ represents
- an optionally substituted C$_1$–C$_{18}$ alkyl group, preferably an optionally substituted C$_1$–C$_6$ alkyl group, more preferably a C$_1$–C$_4$ alkyl group, such as methyl ethyl, propyl, isopropyl, butyl, isobutyl and t-butyl,
- an optionally substituted lower alkenyl group, or
- an optionally substituted lower alkoxy group; or R$^2$ and R$^3$ together represent —(CH$_2$)$_m$— in which m is 3 or 4; and W represents 1 to 4 substituents on the nucleus which may be identical or different and each of which is
- a halogen atom,
- an optionally substituted C$_1$–C$_{10}$ alkyl group,
- an optionally substituted lower alkenyl group,
- an optionally substituted lower alkynyl group,
- an optionally substituted C$_1$–C$_{10}$ alkoxy group,
- an optionally substituted C$_3$–C$_{10}$ cycloalkyl group,
- an optionally substituted aryl group,
- an optionally substituted aryloxy group,
- NR$^8$R$^9$ in which R$^8$ and R$^9$ are each a hydrogen atom, an optionally substituted C$_1$–C$_6$ alkyl group or an optionally substituted phenyl group, or R$^8$ and R$^9$ together with N may form a four- to six-membered ring containing one or two heteroatoms,
- COR$^{10}$ in which R$^{10}$ is a hydrogen atom, an optionally substituted lower alkyl group or an optionally substituted lower alkenyl group,
- COOR$^{11}$ in which R$^{11}$ is a hydrogen atom, an optionally substituted lower alkyl group or an optionally substituted lower alkenyl group,
- a nitro group, or
- a cyano group.

Agriculturally and horticulturally acceptable acid addition salts of the 4-quinolinol derivative represented by the aforementioned general formula (I) mean salts generally usable in agriculture and horticulture, such as hydrochloride, nitrate, sulfate, phosphate and acetate.

The 4-quinolinol derivative represented by the aforementioned general formula (I) may be in the form of hydrate or solvate. Such hydrate and solvate of the compound represented by the general formula (I) are also included in the present invention.

Substituents which optionally present on the 4-quinoline derivative represented by the aforementioned general formula (I) include a halogen atom, such as fluorine, bromine and chlorine, a C$_1$–C$_4$ alkyl group, a C$_1$–C$_4$ alkoxy group, a hydroxyl group, a nitro group, a formyl group, a cyano group and the like.

The term "lower alkyl group" as used herein means an alkyl group containing about 1 to 4 carbon atoms, such as methyl, ethyl, propyl or butyl.

The term "lower alkenyl group" as used herein means an alkenyl group containing about 2 to 4 carbon atoms, such as vinyl, (1- or 2-)propenyl or (1-, 2- or 3-)butenyl.

The term "lower alkynyl group" as used herein means an alkynyl group containing about 2 to 4 carbon atoms, such as ethynyl, (1- or 2-)propynyl or (1-, 2- or 3-)butynyl.

The term "lower alkoxy group" as used herein means an alkoxy group containing about 1 to 4 carbon atoms, such as methoxy, ethoxy, propyloxy or butyloxy.

The term "C$_1$–C$_{18}$ alkyl group" as used herein means an alkyl group, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl or octadecyl.

The term "C$_2$–C$_{18}$ alkenyl group" as used herein means, for example, vinyl, (1- or 2-)propenyl, (1-, 2- or 3-)butenyl, (1-, 2-, 3- or 4-)pentenyl, (1-, 2-, 3-, 4- or 5-)hexenyl, (1-, 2-, 3-, 4-, 5- or 6-)heptenyl, (1-, 2-, 3-, 4-, 5-, 6- or 7-)octenyl, (1-, 2-, 3-, 4-, 5-, 6-, 7- or 8-)nonenyl, (1-, 2-, 3-, 4-, 5-, 6-, 7-, 8- or 9-)decenyl, (1-, 2-, 3-, 4-, 5-, 6-, 7-, 8-, 9- or 10-)undecenyl, (1-, 2-, 3-, 4-, 5-, 6-, 7-, 8-, 9-, 10- or 11-)dodecenyl, (1-, 2-, 3-, 4-, 5-, 6-, 7-, 8-, 9-, 10-, 11- or 12-)tridecenyl, (1-, 2-, 3-, 4-, 5-, 6-, 7-, 8-, 9-, 10-, 11-, 12- or 13-)tetradecenyl, (1-, 2-, 3-, 4-, 5-, 6-, 7-, 8-, 9-, 10-, 11-, 12-, 13- or 14-)pentadecenyl, (1-, 2-, 3-, 4-, 5-, 6-, 7-, 8-, 9-, 10-, 11-, 12-, 13-, 14- or 15-)hexadecenyl, (1-, 2-, 3-, 4-, 5-, 6-, 7-, 8-, 9-, 10-, 11-, 12-, 13-, 14-, 15- or 16-)heptadecenyl, or (1-, 2-, 3-, 4-, 5-, 6-, 7-, 8-, 9-, 10-, 11-, 12-, 13-, 14-, 15-, 16- or 17-)octadecenyl.

The term "C$_3$–C$_{10}$ cycloalkyl group" as used herein means, for example, cyclopropyl, cyclobutyl, cyclopentyl, cyclohexyl, cycloheptyl, cyclooctyl, cyclononyl or cyclodecyl.

The term "C$_1$–C$_{10}$ alkoxy group" as used herein means, for example, methoxy, ethoxy, propyloxy, butyloxy, pentyloxy, hexyloxy, heptyloxy, octyloxy, nonyloxy or decyloxy.

The term "phenyl lower alkyl group" as used herein means a phenylalkyl group having a C$_1$–C$_4$ alkyl moiety, such as benzyl, (1- or 2-)phenylethyl, (1-, 2- or 3-)phenylpropyl or (1-, 2-, 3- or 4-)phenylbutyl.

The term "phenoxy lower alkyl group" as used herein means a phenoxyalkyl group having a C$_1$–C$_4$ alkyl moiety, such as phenoxymethyl, (1- or 2-)phenoxyethyl, (1-, 2- or 3-)phenoxypropyl or (1-, 2-, 3- or 4-)phenoxybutyl.

The following Table 1 specifically illustrates the compounds within the scope of the 4-hydroxyquinoline derivatives represented by the general formula (I) of the present invention.

Abbreviations used in Table 1 and Examples have following meanings.
- iso-C$_3$H$_7$ isopropyl
- t-C$_4$H$_9$ tertiary butyl
- s-C$_4$H$_9$ secondary butyl
- c-C$_5$H$_9$ cyclopentyl
- c-C$_6$H$_{11}$ cyclohexyl
- n-pentyl, normal pentyl

TABLE 1

| compound No. | R¹ | R² | R³ | W |
|---|---|---|---|---|
| 1 | H | $CH_3$ | $CH_3$ | 6-$CH_3$ |
| 2 | $CH_3CO$ | $CH_3$ | $CH_3$ | 6-$CH_3$ |
| 3 | $C_6H_5CO$ | $CH_3$ | $CH_3$ | 6-$CH_3$ |
| 4 | $CH_3OCO$ | $CH_3$ | $CH_3$ | 6-$CH_3$ |
| 5 | H | $CH_3$ | $CH_3$ | 6-$CH_3O$ |
| 6 | $CH_3CO$ | $CH_3$ | $CH_3$ | 6-$CH_3O$ |
| 7 | $C_6H_5CO$ | $CH_3$ | $CH_3$ | 6-$CH_3O$ |
| 8 | $CH_3OCO$ | $CH_3$ | $CH_3$ | 6-$CH_3O$ |
| 9 | H | $CH_3$ | $CH_3$ | 6-$C_2H_5$ |
| 10 | $CH_3CO$ | $CH_3$ | $CH_3$ | 6-$C_2H_5$ |
| 11 | $C_6H_5CO$ | $CH_3$ | $CH_3$ | 6-$C_2H_5$ |
| 12 | $CH_3OCO$ | $CH_3$ | $CH_3$ | 6-$C_2H_5$ |
| 13 | H | $CH_3$ | $CH_3$ | 6-$C_3H_7$ |
| 14 | $CH_3CO$ | $CH_3$ | $CH_3$ | 6-$C_3H_7$ |
| 15 | $C_6H_5CO$ | $CH_3$ | $CH_3$ | 6-$C_3H_7$ |
| 16 | $CH_3OCO$ | $CH_3$ | $CH_3$ | 6-$C_3H_7$ |
| 17 | $(C_2H_5)_2NCO$ | $CH_3$ | $CH_3$ | 6-$C_3H_7$ |
| 18 | H | $CH_3$ | $CH_3$ | 6-iso-$C_3H_7$ |
| 19 | $CH_3CO$ | $CH_3$ | $CH_3$ | 6-iso-$C_3H_7$ |
| 20 | $C_6H_5CO$ | $CH_3$ | $CH_3$ | 6-iso-$C_3H_7$ |
| 21 | $CH_3OCO$ | $CH_3$ | $CH_3$ | 6-iso-$C_3H_7$ |
| 22 | $(C_2H_5)_2NCO$ | $CH_3$ | $CH_3$ | 6-iso-$C_3H_7$ |
| 23 | H | $CH_3$ | $CH_3$ | 6-iso-$C_3H_7O$ |
| 24 | $CH_3CO$ | $CH_3$ | $CH_3$ | 6-iso-$C_3H_7O$ |
| 25 | $C_6H_5CO$ | $CH_3$ | $CH_3$ | 6-iso-$C_3H_7O$ |
| 26 | $CH_3OCO$ | $CH_3$ | $CH_3$ | 6-iso-$C_3H_7O$ |
| 27 | $C_6H_5OCO$ | $CH_3$ | $CH_3$ | 6-iso-$C_3H_7O$ |
| 28 | H | $CH_3$ | $CH_3$ | 6-$C_4H_9$ |
| 29 | $CH_3CO$ | $CH_3$ | $CH_3$ | 6-$C_4H_9$ |
| 30 | $C_2H_5CO$ | $CH_3$ | $CH_3$ | 6-$C_4H_9$ |
| 31 | c-$C_3H_5CO$ | $CH_3$ | $CH_3$ | 6-$C_4H_9$ |
| 32 | t-$C_4H_9CO$ | $CH_3$ | $CH_3$ | 6-$C_4H_9$ |
| 33 | $C_6H_5CO$ | $CH_3$ | $CH_3$ | 6-$C_4H_9$ |
| 34 | 4-$CH_3O$—$C_6H_4CO$ | $CH_3$ | $CH_3$ | 6-$C_4H_9$ |
| 35 | 4-Cl—$C_6H_4CO$ | $CH_3$ | $CH_3$ | 6-$C_4H_9$ |
| 36 | $CH_3OCO$ | $CH_3$ | $CH_3$ | 6-$C_4H_9$ |
| 37 | $C_2H_5OCO$ | $CH_3$ | $CH_3$ | 6-$C_4H_9$ |
| 38 | $C_8H_{17}OCO$ | $CH_3$ | $CH_3$ | 6-$C_4H_9$ |
| 39 | $C_6H_5OCO$ | $CH_3$ | $CH_3$ | 6-$C_4H_9$ |
| 40 | 4-$CH_3O$—$C_6H_4CO$ | $CH_3$ | $CH_3$ | 6-$C_4H_9$ |
| 41 | 4-Cl—$C_6H_4OCO$ | $CH_3$ | $CH_3$ | 6-$C_4H_9$ |
| 42 | $(C_2H_5)_2NCO$ | $CH_3$ | $CH_3$ | 6-$C_4H_9$ |
| 43 | $(C_6H_5)_2NCO$ | $CH_3$ | $CH_3$ | 6-$C_4H_9$ |
| 44 | $CH_3CO$ | $C_2H_5$ | $CH_3$ | 6-$C_4H_9$ |
| 45 | $CH_3CO$ | $C_3H_7$ | $CH_3$ | 6-$C_4H_9$ |
| 46 | $CH_3CO$ | $C_4H_9$ | $CH_3$ | 6-$C_4H_9$ |
| 47 | $CH_3CO$ | $CH_3$ | $C_2H_5$ | 6-$C_4H_9$ |
| 48 | $CH_3CO$ | $CH_3$ | $C_3H_7$ | 6-$C_4H_9$ |
| 49 | $CH_3CO$ | $CH_3$ | $C_4H_9$ | 6-$C_4H_9$ |
| 50 | H | —$(CH_2)_4$— | | 6-$C_4H_9$ |
| 51 | $CH_3CO$ | —$(CH_2)_4$— | | 6-$C_4H_9$ |
| 52 | $C_2H_5CO$ | —$(CH_2)_4$— | | 6-$C_4H_9$ |
| 53 | $C_6H_5CO$ | —$(CH_2)_4$— | | 6-$C_4H_9$ |
| 54 | H | $CH_3$ | $CH_3$ | 6-s-$C_4H_9$ |
| 55 | $CH_3CO$ | $CH_3$ | $CH_3$ | 6-s-$C_4H_9$ |
| 56 | $C_2H_5CO$ | $CH_3$ | $CH_3$ | 6-s-$C_4H_9$ |
| 57 | c-$C_3H_5CO$ | $CH_3$ | $CH_3$ | 6-s-$C_4H_9$ |
| 58 | t-$C_4H_9CO$ | $CH_3$ | $CH_3$ | 6-s-$C_4H_9$ |
| 59 | t-$C_4H_9CH_2CO$ | $CH_3$ | $CH_3$ | 6-s-$C_4H_9$ |
| 60 | $C_8H_{17}CO$ | $CH_3$ | $CH_3$ | 6-s-$C_4H_9$ |
| 61 | $C_6H_5CO$ | $CH_3$ | $CH_3$ | 6-s-$C_4H_9$ |
| 62 | 4-$CH_3O$—$C_6H_4CO$ | $CH_3$ | $CH_3$ | 6-s-$C_4H_9$ |
| 63 | 4-Cl—$C_6H_4CO$ | $CH_3$ | $CH_3$ | 6-s-$C_4H_9$ |
| 64 | 2,6-di-$CH_3O$—$C_6H_3CO$ | $CH_3$ | $CH_3$ | 6-s-$C_4H_9$ |
| 65 | $CH_3OCO$ | $CH_3$ | $CH_3$ | 6-s-$C_4H_9$ |
| 66 | $C_2H_5OCO$ | $CH_3$ | $CH_3$ | 6-s-$C_4H_9$ |
| 67 | $C_8H_{17}OCO$ | $CH_3$ | $CH_3$ | 6-s-$C_4H_9$ |
| 68 | $C_6H_5OCO$ | $CH_3$ | $CH_3$ | 6-s-$C_4H_9$ |
| 69 | 4-$CH_3O$—$C_6H_4OCO$ | $CH_3$ | $CH_3$ | 6-s-$C_4H_9$ |
| 70 | 4-Cl—$C_6H_4OCO$ | $CH_3$ | $CH_3$ | 6-s-$C_4H_9$ |
| 71 | $(CH_3)_2NCO$ | $CH_3$ | $CH_3$ | 6-s-$C_4H_9$ |
| 72 | $(C_2H_5)_2NCO$ | $CH_3$ | $CH_3$ | 6-s-$C_4H_9$ |
| 73 | $CH_3(C_6H_5)NCO$ | $CH_3$ | $CH_3$ | 6-s-$C_4H_9$ |
| 74 | $(C_6H_5)_2NCO$ | $CH_3$ | $CH_3$ | 6-s-$C_4H_9$ |
| 75 | H | $CH_3$ | $CH_3O$ | 6-t-$C_4H_9$ |
| 76 | $CH_3CO$ | $CH_3$ | $CH_3O$ | 6-t-$C_4H_9$ |
| 77 | H | $CH_3$ | $CH_3O$ | 6-s-$C_4H_9$ |
| 78 | $CH_3CO$ | $CH_3$ | $CH_3O$ | 6-s-$C_4H_9$ |
| 79 | $CH_3CO$ | $CH_3$ | $CF_3$ | 6-s-$C_4H_9$ |
| 80 | H | $CH_3$ | $CF_3$ | 6-s-$C_4H_9$ |
| 81 | $CH_3CO$ | $CH_3$ | $CF_3$ | 6-t-$C_4H_9$ |
| 82 | H | $CH_3$ | $CF_3$ | 6-t-$C_4H_9$ |
| 83 | H | $CH_3$ | $CH_3$ | 6-t-$C_4H_9$ |
| 84 | $CH_3CO$ | $CH_3$ | $CH_3$ | 6-t-$C_4H_9$ |
| 85 | $C_2H_5CO$ | $CH_3$ | $CH_3$ | 6-t-$C_4H_9$ |
| 86 | c-$C_3H_5CO$ | $CH_3$ | $CH_3$ | 6-t-$C_4H_9$ |
| 87 | $C_6H_5CO$ | $CH_3$ | $CH_3$ | 6-t-$C_4H_9$ |
| 88 | $CH_3OCO$ | $CH_3$ | $CH_3$ | 6-t-$C_4H_9$ |
| 89 | $C_2H_5OCO$ | $CH_3$ | $CH_3$ | 6-t-$C_4H_9$ |
| 90 | $C_6H_5OCO$ | $CH_3$ | $CH_3$ | 6-t-$C_4H_9$ |
| 91 | $(C_2H_5)_2NCO$ | $CH_3$ | $CH_3$ | 6-t-$C_4H_9$ |
| 92 | H | $CH_3$ | $CH_3$ | 6-iso-$C_4H_9$ |
| 93 | $CH_3CO$ | $CH_3$ | $CH_3$ | 6-iso-$C_4H_9$ |
| 94 | $C_6H_5CO$ | $CH_3$ | $CH_3$ | 6-iso-$C_4H_9$ |
| 95 | $CH_3OCO$ | $CH_3$ | $CH_3$ | 6-iso-$C_4H_9$ |
| 96 | $C_6H_5OCO$ | $CH_3$ | $CH_3$ | 6-iso-$C_4H_9$ |
| 97 | H | $CH_3$ | $CH_3$ | 6-$C_5H_{11}$ |
| 98 | $CH_3CO$ | $CH_3$ | $CH_3$ | 6-$C_5H_{11}$ |
| 99 | $C_6H_5CO$ | $CH_3$ | $CH_3$ | 6-$C_5H_{11}$ |
| 100 | $CH_3OCO$ | $CH_3$ | $CH_3$ | 6-$C_5H_{11}$ |
| 101 | $C_6H_5OCO$ | $CH_3$ | $CH_3$ | 6-$C_5H_{11}$ |
| 102 | H | $CH_3$ | $CH_3$ | 6-c-$C_5H_9$ |
| 103 | $CH_3CO$ | $CH_3$ | $CH_3$ | 6-c-$C_5H_9$ |
| 104 | $C_6H_5CO$ | $CH_3$ | $CH_3$ | 6-c-$C_5H_9$ |
| 105 | $CH_3OCO$ | $CH_3$ | $CH_3$ | 6-c-$C_5H_9$ |
| 106 | $(C_2H_5)_2NCO$ | $CH_3$ | $CH_3$ | 6-c-$C_5H_9$ |
| 107 | H | $CH_3$ | $CH_3$ | 6-$C_6H_{13}$ |
| 108 | $CH_3CO$ | $CH_3$ | $CH_3$ | 6-$C_6H_{13}$ |
| 109 | $C_6H_5CO$ | $CH_3$ | $CH_3$ | 6-$C_6H_{13}$ |
| 110 | $CH_3OCO$ | $CH_3$ | $CH_3$ | 6-$C_6H_{13}$ |
| 111 | H | $CH_3$ | $CH_3$ | 6-c-$C_6H_{11}$ |
| 112 | $CH_3CO$ | $CH_3$ | $CH_3$ | 6-c-$C_6H_{11}$ |
| 113 | $C_2H_5CO$ | $CH_3$ | $CH_3$ | 6-c-$C_6H_{11}$ |
| 114 | $C_6H_5CO$ | $CH_3$ | $CH_3$ | 6-c-$C_6H_{11}$ |
| 115 | 4-$CH_3O$—$C_6H_4CO$ | $CH_3$ | $CH_3$ | 6-c-$C_6H_{11}$ |
| 116 | 4-Cl—$C_6H_4CO$ | $CH_3$ | $CH_3$ | 6-c-$C_6H_{11}$ |
| 117 | $CH_3OCO$ | $CH_3$ | $CH_3$ | 6-c-$C_6H_{11}$ |
| 118 | $C_6H_5CO$ | $CH_3$ | $CH_3$ | 6-c-$C_6H_{11}$ |
| 119 | $(C_2H_5)_2NCO$ | $CH_3$ | $CH_3$ | 6-c-$C_6H_{11}$ |
| 120 | H | $CH_3$ | $CH_3$ | 6-$C_7H_{15}$ |
| 121 | $CH_3CO$ | $CH_3$ | $CH_3$ | 6-$C_7H_{15}$ |
| 122 | $C_6H_5CO$ | $CH_3$ | $CH_3$ | 6-$C_7H_{15}$ |
| 123 | $CH_3OCO$ | $CH_3$ | $CH_3$ | 6-$C_7H_{15}$ |
| 124 | $C_6H_5OCO$ | $CH_3$ | $CH_3$ | 6-$C_7H_{15}$ |
| 125 | H | $CH_3$ | $CH_3$ | 6-$C_8H_{17}$ |
| 126 | $CH_3CO$ | $CH_3$ | $CH_3$ | 6-$C_8H_{17}$ |
| 127 | $C_6H_5CO$ | $CH_3$ | $CH_3$ | 6-$C_8H_{17}$ |
| 128 | $CH_3OCO$ | $CH_3$ | $CH_3$ | 6-$C_8H_{17}$ |
| 129 | $C_2H_5OCO$ | $CH_3$ | $CH_3$ | 6-$C_8H_{17}$ |
| 130 | $C_6H_5OCO$ | $CH_3$ | $CH_3$ | 6-$C_8H_{17}$ |
| 131 | H | $CH_3$ | $CH_3$ | 6-$CF_3$ |
| 132 | $CH_3CO$ | $CH_3$ | $CH_3$ | 6-$CF_3$ |
| 133 | $C_6H_5CO$ | $CH_3$ | $CH_3$ | 6-$CF_3$ |
| 134 | $CH_3OCO$ | $CH_3$ | $CH_3$ | 6-$CF_3$ |
| 135 | H | $CH_3$ | $CH_3$ | 6-$C_6H_5O$ |
| 136 | $CH_3CO$ | $CH_3$ | $CH_3$ | 6-$C_6H_5O$ |
| 137 | $C_6H_5CO$ | $CH_3$ | $CH_3$ | 6-$C_6H_5O$ |
| 138 | H | $CH_3$ | $CH_3$ | 5-$C_2H_5$ |
| 139 | H | $CH_3$ | $CH_3$ | 5-$C_3H_7$ |
| 140 | H | $CH_3$ | $CH_3$ | 7-$C_2H_5$ |
| 141 | H | $CH_3$ | $CH_3$ | 7-$C_3H_7$ |
| 142 | H | $CH_3$ | $CH_3$ | 8-$C_2H_5$ |
| 143 | H | $CH_3$ | $CH_3$ | 8-$C_3H_7$ |
| 144 | H | $CH_3$ | $CH_3$ | 6-$C_4H_9$, 8-$CH_3$ |
| 145 | $CH_3CO$ | $CH_3$ | $CH_3$ | 6-$C_4H_9$, 8-$CH_3$ |
| 146 | H | $CH_3$ | $CH_3$ | 6-$C_4H_9$, 8-F |
| 147 | $CH_3CO$ | $CH_3$ | $CH_3$ | 6-$C_4H_9$, 8-F |
| 148 | H | $CH_3$ | $CH_3$ | 6-$C_4H_9$, 7-$CH_3$ |
| 149 | $CH_3CO$ | $CH_3$ | $CH_3$ | 6-$C_4H_9$, 7-$CH_3$ |
| 150 | H | $CH_3$ | $CH_3$ | 6-$C_4H_9$, 7-F |

TABLE 1-continued

| compound No. | R¹ | R² | R³ | W |
|---|---|---|---|---|
| 151 | CH₃CO | CH₃ | CH₃ | 6-C₄H₉, 7-F. |
| 152 | H | —(CH₂)₃— | | 6-s-C₄H₉ |
| 153 | CH₃CO | —(CH₂)₃— | | 6-s-C₄H₉ |
| 154 | H | CH₃ | CH₃ | 6-N(CH₂CH₃)₂ |
| 155 | CH₃CO | CH₃ | CH₃ | 6-N(CH₂CH₃)₂ |
| 156 | H | CH₃ | CH₃ | 6-Morpholino |
| 157 | CH₃CO | CH₃ | CH₃ | 6-Morpholino |
| 158 | H | —(CH₂)₄— | | 6-iso-C₄H₉ |
| 159 | CH₃CO | —(CH₂)₄— | | 6-iso-C₄H₉ |
| 160 | C₂H₅CO | —(CH₂)₄— | | 6-iso-C₄H₉ |
| 161 | C₆H₅CO | —(CH₂)₄— | | 6-iso-C₄H₉ |
| 162 | H | —(CH₂)₄— | | 6-s-C₄H₉ |
| 163 | CH₃CO | —(CH₂)₄— | | 6-s-C₄H₉ |
| 164 | C₂H₅CO | —(CH₂)₄— | | 6-s-C₄H₉ |
| 165 | C₆H₅CO | —(CH₂)₄— | | 6-s-C₄H₉ |
| 166 | H | —(CH₂)₄— | | 6-N(CH₃)₂ |
| 167 | CH₃CO | —(CH₂)₄— | | 6-N(CH₃)₂ |
| 168 | C₂H₅CO | —(CH₂)₄— | | 6-N(CH₃)₂ |
| 169 | C₆H₅CO | —(CH₂)₄— | | 6-N(CH₃)₂ |
| 170 | c-C₆H₁₁CO | CH₃ | CH₃ | 6-s-C₄H₉ |
| 171 | 4-NO₂—C₆H₄CO | CH₃ | CH₃ | 6-s-C₄H₉ |
| 172 | C₆H₅CH₂CO | CH₃ | CH₃ | 6-s-C₄H₉ |
| 173 | C₆H₁₁CO | CH₃ | CH₃ | 6-s-C₄H₉ |
| 174 | C₆H₁₃CO | CH₃ | CH₃ | 6-s-C₄H₉ |
| 175 | CH₂=CHCH₂CO | CH₃ | CH₃ | 6-s-C₄H₉ |
| 176 | iso-C₄H₉CO | CH₃ | CH₃ | 6-s-C₄H₉ |
| 177 | 2,6-diCl—C₆H₃CO | CH₃ | CH₃ | 6-s-C₄H₉ |
| 178 | H | CH₃ | CH₃ | 6-(1-c-pentenyl) |
| 179 | C₄H₉OCO | CH₃ | CH₃ | 6-s-C₄H₉ |
| 180 | C₇H₁₅CO | CH₃ | CH₃ | 6-s-C₄H₉ |
| 181 | H | CH₃ | CH₃ | 6-Br |
| 182 | CH₃CO | CH₃ | CH₃ | 5-C₂H₅ |
| 183 | CH₃CO | CH₃ | CH₃ | 7-C₂H₅ |
| 184 | CH₃CO | CH₃ | CH₃ | 8-C₂H₅ |
| 185 | CH₃CO | CH₃ | CH₃ | 6-Br |
| 186 | H | CH₃ | CH₃ | 6-C₄H₉, 8-Br |
| 187 | CH₃CO | CH₃ | CH₃ | 6-C₄H₉, 8-Br |
| 188 | H | CH₃ | C₈H₁₇ | 6-s-C₄H₉ |
| 189 | CH₃CO | CH₃ | C₈H₁₇ | 6-s-C₄H₉ |
| 190 | H | CH₃ | CH₃ | 6-Br, 8-CH₃ |
| 191 | H | CH₃ | CH₃ | 5-CH₃, 6-Br |
| 192 | H | CH₃ | CH₃ | 6-Br, 7-CH₃ |
| 193 | H | CH₃ | CH₃ | 6-Br, 8-F |
| 194 | H | CH₃ | CH₃ | 6-F, 8-CH₃ |
| 195 | CH₃CO | CH₃ | CH₃ | 6-Br, 8-CH₃ |
| 196 | CH₃CO | CH₃ | CH₃ | 6-Br, 7-CH₃ |
| 197 | CH₃CO | CH₃ | CH₃ | 5-CH₃, 6-Br |
| 198 | CH₃CO | CH₃ | CH₃ | 6-F, 8-CH₃ |
| 199 | H | CH₃ | CH₃ | 6-CH₃CH=C(CH₃) |
| 200 | CH₃CO | CH₃ | CH₃ | 6-CH₃CH=C(CH₃) |
| 201 | H | CH₃ | CH₃ | 5-CH₃, 6-s-C₄H₉ |
| 202 | CH₃CO | CH₃ | CH₃ | 5-CH₃, 6-s-C₄H₉ |
| 203 | H | CH₃ | CH₃ | 6-s-C₄H₉, 7-CH₃ |
| 204 | CH₃CO | CH₃ | CH₃ | 6-s-C₄H₉, 7-CH₃ |
| 205 | H | CH₃ | CH₃ | 6-s-C₄H₉, 8-CH₃ |
| 206 | CH₃CO | CH₃ | CH₃ | 6-s-C₄H₉, 8-CH₃ |
| 207 | H | CH₃ | CH₃ | 5-F, 6-s-C₄H₉ |
| 208 | CH₃CO | CH₃ | CH₃ | 5-F, 6-s-C₄H₉ |
| 209 | H | CH₃ | CH₃ | 6-s-C₄H₉, 7-F |
| 210 | CH₃CO | CH₃ | CH₃ | 6-s-C₄H₉, 7-F |
| 211 | H | CH₃ | CH₃ | 6-s-C₄H₉, 8-F |
| 212 | CH₃CO | CH₃ | CH₃ | 6-s-C₄H₉, 8-F |
| 213 | H | CH₃ | CH₃ | 6-s-C₄H₉, 8-Cl |
| 214 | CH₃CO | CH₃ | CH₃ | 6-s-C₄H₉, 8-Cl |
| 215 | H | CH₃ | CH₃ | 6-n-C₄H₉, 8-Cl |
| 216 | CH₃CO | CH₃ | CH₃ | 6-n-C₄H₉, 8-Cl |
| 217 | H | CH₃ | CH₃ | 6-t-C₄H₉, 8-Cl |
| 218 | CH₃CO | CH₃ | CH₃ | 6-t-C₄H₉, 8-Cl |
| 219 | H | CH₃ | CH₃ | 6-s-C₄H₉, 8-CH₃O |
| 220 | CH₃CO | CH₃ | CH₃ | 6-s-C₄H₉, 8-CH₃O |
| 221 | H | CH₃ | CH₃ | 6-n-C₄H₉, 8-CH₃O |
| 222 | CH₃CO | CH₃ | CH₃ | 6-n-C₄H₉, 8-CH₃O |
| 223 | H | CH₃ | CH₃ | 6-t-C₄H₉, 8-CH₃O |
| 224 | CH₃CO | CH₃ | CH₃ | 6-t-C₄H₉, 8-CH₃O |
| 225 | H | CH₃ | CH₃ | 6-s-C₄H₉, 5-Cl |
| 226 | CH₃CO | CH₃ | CH₃ | 6-s-C₄H₉, 5-Cl |
| 227 | H | CH₃ | CH₃ | 6-t-C₄H₉, 5-Cl |
| 228 | CH₃CO | CH₃ | CH₃ | 6-t-C₄H₉, 5-Cl |
| 229 | H | CH₃ | CH₃ | 6-n-C₄H₉, 5-Cl |
| 230 | CH₃CO | CH₃ | CH₃ | 6-n-C₄H₉, 5-Cl |
| 231 | H | CH₃ | CH₃ | 6-s-C₄H₉, 5-CH₃O |
| 232 | CH₃CO | CH₃ | CH₃ | 6-s-C₄H₉, 5-CH₃O |
| 233 | H | CH₃ | CH₃ | 6-n-C₄H₉, 5-CH₃O |
| 234 | CH₃CO | CH₃ | CH₃ | 6-n-C₄H₉, 5-CH₃O |
| 235 | H | CH₃ | CH₃ | 6-t-C₄H₉, 5-OCH₃ |
| 236 | CH₃CO | CH₃ | CH₃ | 6-t-C₄H₉, 5-OCH₃ |
| 237 | H | CH₃ | CH₃ | 6-s-C₄H₉, 7-Cl |
| 238 | CH₃CO | CH₃ | CH₃ | 6-s-C₄H₉, 7-Cl |
| 239 | H | CH₃ | CH₃ | 6-t-C₄H₉, 7-Cl |
| 240 | CH₃CO | CH₃ | CH₃ | 6-t-C₄H₉, 7-Cl |
| 241 | H | CH₃ | CH₃ | 6-n-C₄H₉, 7-Cl |
| 242 | CH₃CO | CH₃ | CH₃ | 6-n-C₄H₉, 7-Cl |
| 243 | H | CH₃ | CH₃ | 6-s-C₄H₉, 7-CH₃O |
| 244 | CH₃CO | CH₃ | CH₃ | 6-s-C₄H₉, 7-CH₃O |
| 245 | H | CH₃ | CH₃ | 6-n-C₄H₉, 7-CH₃O |
| 246 | CH₃CO | CH₃ | CH₃ | 6-n-C₄H₉, 7-CH₃O |
| 247 | H | CH₃ | CH₃ | 6-t-C₄H₉, 7-CH₃O |
| 248 | CH₃CO | CH₃ | CH₃ | 6-t-C₄H₉, 7-CH₃O |
| 249 | H | CH₃ | CH₃ | 6-t-C₄H₉, 8-CH₃ |
| 250 | CH₃CO | CH₃ | CH₃ | 6-t-C₄H₉, 8-CH₃ |
| 251 | H | CH₃ | CH₃ | 6-t-C₄H₉, 8-F |
| 252 | CH₃CO | CH₃ | CH₃ | 6-t-C₄H₉, 8-F |
| 253 | H | CH₃ | CH₃ | 6-t-C₄H₉, 5-CH₃ |
| 254 | CH₃CO | CH₃ | CH₃ | 6-t-C₄H₉, 5-CH₃ |
| 255 | H | CH₃ | CH₃ | 6-t-C₄H₉, 5-F |
| 256 | CH₃CO | CH₃ | CH₃ | 6-t-C₄H₉, 5-F |
| 257 | H | CH₃ | CH₃ | 6-t-C₄H₉, 7-CH₃ |
| 258 | CH₃CO | CH₃ | CH₃ | 6-t-C₄H₉, 7-CH₃ |
| 259 | H | CH₃ | CH₃ | 6-t-C₄H₉, 7-F |
| 260 | CH₃CO | CH₃ | CH₃ | 6-t-C₄H₉, 7-F |
| 261 | H | CH₃ | CH₃ | 6-CH₃, 8-CH₃ |
| 262 | CH₃CO | CH₃ | CH₃ | 6-CH₃, 8-CH₃ |
| 263 | H | CH₃ | CH₃ | 5-CH₃, 6-CH₃ |
| 264 | CH₃CO | CH₃ | CH₃ | 5-CH₃, 6-CH₃ |
| 265 | H | CH₃ | CH₃ | 6-CH₃, 7-CH₃ |
| 266 | CH₃CO | CH₃ | CH₃ | 6-CH₃, 7-CH₃ |
| 267 | H | CH₃ | CH₃ | 6-C₂H₅, 8-C₂H₅ |
| 268 | CH₃CO | CH₃ | CH₃ | 6-C₂H₅, 8-C₂H₅ |
| 269 | H | CH₃ | CH₃ | 5-C₂H₅, 6-C₂H₅ |
| 270 | CH₃CO | CH₃ | CH₃ | 5-C₂H₅, 6-C₂H₅ |
| 271 | H | CH₃ | CH₃ | 6-C₂H₅, 7-C₂H₅ |
| 272 | CH₃CO | CH₃ | CH₃ | 6-C₂H₅, 7-C₂H₅ |
| 273 | H | CH₃ | CH₃ | 6-iso-C₃H₇, 8-iso-C₃H₇ |
| 274 | CH₃CO | CH₃ | CH₃ | 6-iso-C₃H₇, 8-iso-C₃H₇ |
| 275 | H | CH₃ | CH₃ | 5-iso-C₃H₇, 6-iso-C₃H₇ |
| 276 | CH₃CO | CH₃ | CH₃ | 5-iso-C₃H₇, 6-iso-C₃H₇ |
| 277 | H | CH₃ | CH₃ | 6-iso-C₃H₇, 7-iso-C₃H₇ |
| 278 | CH₃CO | CH₃ | CH₃ | 6-iso-C₃H₇, 7-iso-C₃H₇ |
| 279 | H | CH₃ | CH₃ | 6-s-C₄H₉, 8-s-C₄H₉ |
| 280 | CH₃CO | CH₃ | CH₃ | 6-s-C₄H₉, 8-s-C₄H₉ |
| 281 | H | CH₃ | CH₃ | 5-s-C₄H₉, 6-s-C₄H₉ |
| 282 | CH₃CO | CH₃ | CH₃ | 5-s-C₄H₉, 6-s-C₄H₉ |
| 283 | H | CH₃ | CH₃ | 6-s-C₄H₉, 7-s-C₄H₉ |
| 284 | CH₃CO | CH₃ | CH₃ | 6-s-C₄H₉, 7-s-C₄H₉ |
| 285 | H | CH₃ | CH₃ | 6-t-C₄H₉, 8-t-C₄H₉ |
| 286 | CH₃CO | CH₃ | CH₃ | 6-t-C₄H₉, 8-t-C₄H₉ |

TABLE 1-continued

| compound No. | R¹ | R² | R³ | W |
|---|---|---|---|---|
| 287 | H | CH₃ | CH₃ | 5-t-C₄H₉, 6-t-C₄H₉ |
| 288 | CH₃CO | CH₃ | CH₃ | 5-t-C₄H₉, 6-t-C₄H₉ |
| 289 | H | CH₃ | CH₃ | 6-t-C₄H₉, 7-t-C₄H₉ |
| 290 | CH₃CO | CH₃ | CH₃ | 6-t-C₄H₉, 7-t-C₄H₉ |
| 291 | H | CH₃ | CH₃ | 6-c-C₃H₄(CH₃) |
| 292 | CH₃CO | CH₃ | CH₃ | 6-c-C₃H₄(CH₃) |
| 293 | H | CH₃ | CH₃ | 6-c-C₃H₄(CH₃), 8-CH₃ |
| 294 | CH₃CO | CH₃ | CH₃ | 6-c-C₃H₄(CH₃), 8-CH₃ |
| 295 | H | CH₃ | CH₃ | 6-c-C₃H₄(CH₃), 8-Cl |
| 296 | CH₃CO | CH₃ | CH₃ | 6-c-C₃H₄(CH₃), 8-Cl |
| 297 | H | CH₃ | CH₃ | 6-c-C₃H₅—CH₂ |
| 298 | CH₃CO | CH₃ | CH₃ | 6-c-C₃H₅—CH₂ |
| 299 | H | CH₃ | CH₃ | 6-c-C₃H₅—CH₂, 8-CH₃ |
| 300 | CH₃CO | CH₃ | CH₃ | 6-c-C₃H₅—CH₂, 8-CH₃ |
| 301 | H | CH₃ | CH₃ | 6-c-C₃H₅—CH₂, 8-Cl |
| 302 | CH₃CO | CH₃ | CH₃ | 6-c-C₃H₅—CH₂, 8-Cl |
| 303 | H | CH₃ | CH₃ | 6-C₆H₅ |
| 304 | CH₃CO | CH₃ | CH₃ | 6-C₆H₅ |
| 305 | H | CH₃ | CH₃ | 6-C₆H₅, 8-CH₃ |
| 306 | CH₃CO | CH₃ | CH₃ | 6-C₆H₅, 8-CH₃ |
| 307 | H | CH₃ | CH₃ | 6-C₆H₅, 8-Cl |
| 308 | CH₃CO | CH₃ | CH₃ | 6-C₆H₅, 8-Cl |
| 309 | H | CH₃ | CH₃ | 6-(p-Cl)—C₆H₄ |
| 310 | CH₃CO | CH₃ | CH₃ | 6-(p-Cl)—C₆H₄ |
| 311 | H | CH₃ | CH₃ | 6-(p-Cl)—C₆H₄, 8-CH₃ |
| 312 | CH₃CO | CH₃ | CH₃ | 6-(p-Cl)—C₆H₄, 8-CH₃ |
| 313 | H | CH₃ | CH₃ | 6-(p-Cl)—C₆H₄, 8-Cl |
| 314 | CH₃CO | CH₃ | CH₃ | 6-(p-Cl)—C₆H₄, 8-Cl |
| 315 | H | CH₃ | CH₃ | 6-(p-CH₃)—C₆H₄ |
| 316 | CH₃CO | CH₃ | CH₃ | 6-(p-CH₃)—C₆H₄ |
| 317 | H | CH₃ | CH₃ | 6-(p-CH₃)—C₆H₄, 8-CH₃ |
| 318 | CH₃CO | CH₃ | CH₃ | 6-(p-CH₃)—C₆H₄, 8-CH₃ |
| 319 | H | CH₃ | CH₃ | 6-(p-CH₃)—C₆H₄, 8-Cl |
| 320 | CH₃CO | CH₃ | CH₃ | 6-(p-CH₃)—C₆H₄, 8-Cl |
| 321 | H | CH₃ | CH₃ | 6-C₆H₅—CH₂ |
| 322 | CH₃CO | CH₃ | CH₃ | 6-C₆H₅CH₂ |
| 323 | H | CH₃ | CH₃ | 6-C₆H₅—CH₂, 8-CH₃ |
| 324 | CH₃CO | CH₃ | CH₃ | 6-C₆H₅—CH₂, 8-CH₃ |
| 325 | H | CH₃ | CH₃ | 6-C₆H₅—CH₂, 8-Cl |
| 326 | CH₃CO | CH₃ | CH₃ | 6-C₆H₅—CH₂, 8-Cl |
| 327 | H | CH₃ | CH₃ | 6-C₆H₅—C(CH₃)₂ |
| 328 | CH₃CO | CH₃ | CH₃ | 6-C₆H₅—C(CH₃)₂ |
| 329 | H | CH₃ | CH₃ | 6-C₆H₅—C(CH₃)₂, 8-CH₃ |
| 330 | CH₃CO | CH₃ | CH₃ | 6-C₆H₅—C(CH₃)₂, 8-CH₃ |
| 331 | H | CH₃ | CH₃ | 6-C₆H₅—C(CH₃)₂, 8-Cl |
| 332 | CH₃CO | CH₃ | CH₃ | 6-C₆H₅—C(CH₃)₂, 8-Cl |
| 333 | H | CH₃ | CH₃ | 6-t-C₄H₉—CH₂ |
| 334 | CH₃CO | CH₃ | CH₃ | 6-t-C₄H₉—CH₂ |
| 335 | H | CH₃ | CH₃ | 6-t-C₄H₉—CH₂, 8-CH₃ |
| 336 | CH₃CO | CH₃ | CH₃ | 6-t-C₄H₉—CH₂, 8-CH₃ |
| 337 | H | CH₃ | CH₃ | 6-t-C₄H₉—CH₂, 8-Cl |
| 338 | CH₃CO | CH₃ | CH₃ | 6-t-C₄H₉—CH₂, 8-Cl |
| 339 | H | CH₃ | CH₃ | 6-s-C₄H₉, 8-CH₂OH |
| 340 | CH₃CO | CH₃ | CH₃ | 6-s-C₄H₉, 8-CH₂OH |
| 341 | H | CH₃ | CH₃ | 6-t-C₄H₉, 8-CH₂OH |
| 342 | CH₃CO | CH₃ | CH₃ | 6-t-C₄H₉, 8-CH₂OH |
| 343 | H | CH₃ | CH₃ | 6-s-C₄H₉, 8-CH₂Cl |
| 344 | CH₃CO | CH₃ | CH₃ | 6-s-C₄H₉, 8-CH₂Cl |
| 345 | H | CH₃ | CH₃ | 6-t-C₄H₉, 8-CH₂Cl |
| 346 | CH₃CO | CH₃ | CH₃ | 6-t-C₄H₉, 8-CH₂Cl |
| 347 | H | CH₃ | CH₃ | 6-s-C₄H₉, 8-C₂H₅ |
| 348 | CH₃CO | CH₃ | CH₃ | 6-s-C₄H₉, 8-C₂H₅ |
| 349 | H | CH₃ | CH₃ | 6-t-C₄H₉, 8-C₂H₅ |
| 350 | CH₃CO | CH₃ | CH₃ | 6-t-C₄H₉, 8-C₂H₅ |
| 351 | H | CH₃ | CH₃ | 6-c-C₅H₉, 8-CH₃ |
| 352 | CH₃CO | CH₃ | CH₃ | 6-c-C₅H₉, 8-CH₃ |
| 353 | H | CH₃ | CH₃ | 6-c-C₅H₉, 8-Cl |
| 354 | CH₃CO | CH₃ | CH₃ | 6-c-C₅H₉, 8-Cl |
| 355 | H | CH₃ | CH₃ | 6-s-C₄H₉, 8-CHO |
| 356 | CH₃CO | CH₃ | CH₃ | 6-s-C₄H₉, 8-CHO |
| 357 | H | CH₃ | CH₃ | 6-t-C₄H₉, 8-CHO |
| 358 | CH₃CO | CH₃ | CH₃ | 6-t-C₄H₉, 8-CHO |
| 359 | H | CH₃ | CH₃ | 6-CH₃CH=C(CH₃), 8-CH₃ |
| 360 | CH₃CO | CH₃ | CH₃ | 6-CH₃CH=C(CH₃), 8-CH₃ |
| 361 | H | CH₃ | CH₃ | 6-CH₃CH=C(CH₃), 8-F |
| 362 | CH₃CO | CH₃ | CH₃ | 6-CH₃CH=C(CH₃), 8-F |
| 363 | H | CH₃ | CH₃ | 6-s-C₄H₉, 8-CN |
| 364 | CH₃CO | CH₃ | CH₃ | 6-s-C₄H₉, 8-CN |
| 365 | H | CH₃ | CH₃ | 6-t-C₄H₉, 8-CN |
| 366 | CH₃CO | CH₃ | CH₃ | 6-t-C₄H₉, 8-CN |
| 367 | H | CH₃ | CH₃ | 6-s-C₄H₉, 8-NO₂ |
| 368 | CH₃CO | CH₃ | CH₃ | 6-s-C₄H₉, 8-NO₂ |
| 369 | H | CH₃ | CH₃ | 6-t-C₄H₉, 8-NO₂ |
| 370 | CH₃CO | CH₃ | CH₃ | 6-t-C₄H₉, 8-NO₂ |
| 371 | H | CH₃ | CH₃ | 6-s-C₄H₉, 8-CH₃OCO |

TABLE 1-continued

| compound No. | R¹ | R² | R³ | W |
|---|---|---|---|---|
| 372 | CH₃CO | CH₃ | CH₃ | 6-s-C₄H₉, 8-CH₃OCO |
| 373 | H | CH₃ | CH₃ | 6-t-C₄H₉, 8-CH₃OCO |
| 374 | CH₃CO | CH₃ | CH₃ | 6-t-C₄H₉, 8-CH₃OCO |

Compounds of the general formula (I)' which comprise a part of 4-quinolinol derivatives represented by the general formula (I) can be prepared by the known method as described in JP-03128355A according to the following scheme.

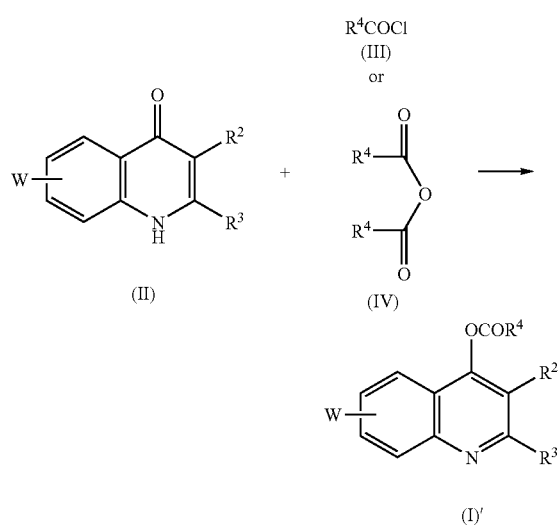

Thus, a compound of the general formula (I)' was synthesized by reacting a compound represented by the general formula (II) with a reagent represented by the general formula (III) or (IV) in the presence or absence of a base and by, if necessary, replacing a substituent of the thus obtained compound with a desired substituent. In the above formulae, $R^1$ to $R^4$ and W are as defined above. Example of the usable base includes organic amines, such as triethylamine and pyridine, or inorganic alkalis, such as sodium carbonate, potassium carbonate and sodium hydride. A compound of the general formula (II) as one of the starting materials was synthesized by a known method as described in J. Am. Chem. Soc., 70, 2402 (1948); Tetrahedron Lett., 27, 5323 (1986) using as a starting material, a substituted aniline which was commercially available or prepared by a known method. And, the reagent represented by the general formula (III) or (IV) is desirably used in an amount of 1 to 50 equivalents, preferably 1 to 10 equivalents with respect to the compound of the general formula (II). The reaction can be carried out in an inert organic solvent, such as dimethylformamide or dimethyl sulfoxide, at the temperature ranging from 0 to 140° C.

Compounds represented by the aforementioned general formula (I) have an excellent fungicidal effect against blast of rice, brown spot of rice, powdery mildew of *Cucurbitaceae*, anthracnose of potato and the like.

When the present compound represented by the general formula (I) is used as an active ingredient of an agricultural and horticultural fungicide, it can be used as such. However, the present compound is generally used in any formulation, such as emulsifiable concentrate, solution, wettable powder, dust formulation, granule, oil solution, aerosol or flowable, which is prepared by combining the present compound with suitable adjuvants, such as solid carrier, liquid carrier, gaseous carrier, surfactant, dispersant and other additives.

Example of the solid carrier includes talc, bentonite, clay, kaolin, diatomaceous earth, vermiculite, white carbon, calcium carbonate and the like. Example of the liquid carrier includes alcohols, such as methanol, n-hexanol and ethylene glycol; ketones, such as acetone, methyl ethyl ketone and cyclohexanone; aliphatic hydrocarbons, such as n-hexane, kerosine and kerosene; aromatic hydrocarbons, such as toluene, xylene and methylnaphthalene; ethers, such as diethyl ether, dioxane and tetrahydrofuran; esters, such as ethyl acetate; nitriles, such as acetonitrile and isobutyronitrile; acid amides, such as dimethylformamide and dimethylacetamide; vegetable oils, such as soybean oil and cottonseed oil; dimethyl sulfoxide; water; and the like. And, example of the gaseous carrier includes LPG, air, nitrogen, carbon dioxide gas, dimethyl ether and the like.

Example of the surfactant or dispersant used for emulsification, dispersion and wetting includes alkyl sulfate esters, alkyl(aryl) sulfonate salts, polyoxyalkylene alkyl(aryl) ethers, polyhydric alcohol esters, lignin sulfonate salts and the like.

And, example of the adjuvant used for improving properties of a formulation includes carboxymethylcellulose, gum arabic, polyethylene glycol, calcium stearate and the like.

The above carrier, surfactant, dispersant and adjuvant may be used alone or in combination, if necessary.

Suitable amount of the active ingredient is generally 1 to 75% by weight in emulsifiable concentrate, generally 0.3 to 25% by weight in dust formulation, generally 1 to 90% by weight in wettable powder, or generally 0.5 to 10% by weight in granule.

Each of these formulations may be used as such or after dilution. Further, each of these formulations may be used in admixture with any other-fungicide, insecticide, acaricide, herbicide, plant growth regulator, fertilizer and the like.

The application methods of the agricultural and horticultural fungicide of the present invention includes foliar application, paddy water application, soil treatment, nursery box application, seed disinfection and the like. Other application methods which are generally employed by those skilled in the art, however, can also show the desired effect of the present invention.

EXAMPLES

Syntheses of the 4-quinolinol derivatives represented by the general formula (I) will be specifically illustrated by way of the following examples which are not intended to limit the invention.

Example 1

Synthesis of 4-hydroxy-2,3-dimethyl-6-n-pentyl-quinoline (Compound No. 97)

1.63 Grams of 4-n-pentylaniline and 1.44 g of ethyl 2-methylacetoacetate were refluxed in benzene in the presence of a Lewis acid catalyst for 3 hours. The reaction mixture was washed with a saturated sodium hydrogencarbonate solution and a saturated brine and dried over anhydrous sodium sulfate. After the solvent was evaporated, the resultant intermediate was refluxed in diphenyl ether for 30 minutes and allowed to cool to produce precipitates, which were collected by filtration under reduced pressure to obtain 1.01 g of 4-hydroxy-2,3-dimethyl-6-n-pentyl-quinoline (yield 42%). Its NMR spectral data are shown in the following Table 2.

Example 2 to 9

The following compounds were synthesized in the same way as that described in Example 1. NMR spectral data of the thus-obtained compounds are shown in the following Table 2.

Example 2

Compound No. 107 (yield 64%)

Example 3

Compound No. 111 (yield 56%)

Example 4

Compound No. 125 (yield 22%)

Example 5

Compound No. 131 (yield 25%)

Example 6

Compound No. 135 (yield 24%)

Example 7

Compound No. 152 (yield 34%)

Example 8

Compound No. 154 (yield 52%)

Example 9

Compound No. 156 (yield 52%)

Example 10

Synthesis of
4-acetoxy-2-3-dimethyl-6-n-pentyl-qunoline
(Compound No. 98)

100 Milligrams of 4-hydroxy-2,3-dimethyl-6-n-pentyl-quinoline (Compound No. 97) was stirred in 2 ml of acetic anhydride at 120° C. for 4 hours. After the solvent was evaporated, 20 ml of ethyl acetate was added and the reaction mixture was washed with an aqueous saturated sodium hydrogencarbonate solution and a saturated brine and dried over anhydrous sodium sulfate. After the solvent was evaporated under reduced pressure, the resultant crude product was purified by column chromatography on silica gel (WAKOGEL® C-100) eluting with n-hexane/ethyl acetate (5:1) to obtain 87.4 mg of 4-acetoxy-2,3-dimethyl-6-n-pentyl-quinoline (yield 74%). Its NMR spectral data are shown in the following Table 2.

Examples 11 to 18

The following compounds were synthesized in the same way as that described in Example 10. NMR spectral data of the thus-obtained compounds are shown in the following Table 2.

Example 11

Compound No. 108 (yield 62%)

Example 12

Compound No. 112 (yield 68%)

Example 13

Compound No. 126 (yield 74%)

Example 14

Compound No. 132 (yield 8%)

Example 15

Compound No. 136 (yield 76%)

Example 16

Compound No. 153 (yield 59%)

Example 17

Compound No. 155 (yield 94%)

Example 18

Compound No. 157 (yield 87%)

Example 19

Synthesis of 4-acetoxy-6-(2-buten-2-yl)-2,3,8-trimethylquinoline (Compound No. 360)

26.6 Grams of 6-bromo-4-hydroxy-2,3,8-trimethylquinoline synthesized in the same way as that described in Example 1 was suspended in 70 ml of dimethylformamide, to which 4.4 g of 60% sodium hydride was added under cooling with ice and then the mixture was stirred at room temperature for 30 minutes. 19 Grams of benzyl bromide was added dropwise to the reaction mixture under cooling with ice and the mixture was allowed to react at room temperature overnight. After 50 ml of water was added, the reaction mixture was extracted with ethyl acetate and the organic layer was washed with a saturated brine and dried over anhydrous sodium sulfate overnight. After the solvent was evaporated under reduced pressure, the resultant crude product was purified by column chromatography on silica gel (WAKOGEL® C-200) eluting with n-hexane/ethyl acetate (6:1) to obtain 24.3 g of 4-benzyloxy-6-bromo-2,3,8-trimethylquinoline.

4 Grams of the thus-obtained 4-benzyloxy-6-bromo-2,3,8-trimethylquinoline was dissolved in 40 ml of anhydrous tetrahydrofuran and cooled to −78° C., to which 5 ml of a 2.5 M solution of n-butyllithium in n-hexane was added dropwise and the mixture was stirred for 10 minutes. A solution of 1.2 g of 2-butanone dissolved in 4 ml of anhydrous tetrahydrofuran was added dropwise to the reaction mixture, which was then stirred at 0° C. for 20 minutes. After 30 ml of water was added, the reaction mixture was extracted with ethyl acetate and the organic layer was washed with a saturated brine and dried over anhydrous sodium sulfate overnight. After the solvent was evaporated under reduced pressure, the residue was purified by column chromatography on silica gel (WAKOGEL® C-200) eluting with n-hexane/ethyl acetate (7:1) to obtain 3.5 g of 4-benzyloxy-6-(2-hydroxybutyl-2-yl)-2,3,8-trimethylquinoline.

To 2.8 g of the thus-obtained 4-benzyloxy-6-(2-hydroxybutyl-2-yl)-2,3,8-trimethylquinoline was added 10 ml of 20% sulfuric acid and the mixture was stirred at 100° C. for 80 minutes. The reaction mixture was cooled to room temperature and then neutralized with an aqueous saturated sodium carbonate solution. Precipitates were washed with water and n-hexane and then dried under reduced pressure to obtain 2.3 g of a crude product. 2.0 Grams of the crude product was suspended in 10 ml of dimethylformamide, to which 0.37 g of 60% sodium hydride was added under cooling with ice. After stirring at room temperature for 30 minutes, 0.72 g of acetyl chloride was added dropwise under cooling with ice and the mixture was stirred at room temperature for 20 hours. After 15 ml of water was added, the reaction mixture was stirred and then extracted with ethyl acetate. The organic layer was washed with a saturated brine and then dried over anhydrous sodium sulfate overnight. After the solvent was evaporated under reduced pressure, the crude product was purified by column chromatography on silica gel (WAKOGEL® C-200) eluting with n-hexane/ethyl acetate (9:1) to obtain 1.6 g of 4-acetoxy-6-(2-buten-2-yl)-2,3,8-trimethylquinoline (yield 42%). Its NMR spectral data are shown in the following Table 2.

Example 20

Synthesis of 4-acetoxy-6-(2-buten-2-yl)-8-fluoro-2,3-dimethylquinoline (Compound No. 362)

4-Acetoxy-6-(2-buten-2-yl)-8-fluoro-2,3-dimethylquinoline was synthesized in the same way as that described in Example 19 using 6-bromo-4-hydroxy-8-fluoro-2,3-dimethylquinoline as a starting material (yield 17%). NMR spectral data of the thus-obtained compounds are shown in the following Table 2.

Example 21

Synthesis of 4-acetoxy-6-s-butyl-2,3,8-trimethylquinoline (Compound No. 206)

To 0.41 g of 4-acetoxy-6-(2-buten-2-yl)-2,3,8-trimethylquinoline obtained in the same way as that described in Example 19 and 0.06 g of 10% palladium-carbon, 6 ml of methanol was added and hydrogen was passed therethrough to react for 16 hours at room temperature with stirring. The reaction mixture was filtered and the residue was washed twice with 2 ml of methanol. The solvent was evaporated under reduced pressure to obtain 0.37 g of 4-acetoxy-6-s-butyl-2,3,8-trimethylquinoline (yield 90%). Its NMR spectral data are shown in the following Table 2.

Example 22

Synthesis of 4-acetoxy-6-s-butyl-8-fluoro-2,3-dimethylquinoline (Compound No. 212)

0.27 Grams of 4-acetoxy-6-s-butyl-8-fluoro-2,3-dimethylquinoline was obtained using 0.37 g of 4-acetoxy-6-(2-buten-2-yl)-8-fluoro-2,3-dimethylquinoline obtained in Example 20 as a starting material in the same way as that described in Example 21 (yield 72%). Its NMR spectral data are shown in the following Table 2.

Example 23

Synthesis of 4-acetoxy-6-c-pentyl-8-methyl-2,3-dimethylquinoline (Compound No. 352)

4-Acetoxy-6-c-pentyl-8-methyl-2,3-dimethylquinoline was obtained in the same way as that described in Example 21 (yield 37%).

Example 24

Synthesis of 4-acetoxy-6-s-butyl-8-chloro-2,3-dimethylquinoline (Compound No. 214)

4.9 Grams of 4-s-butyl-aniline was dissolved in dimethylformamide, to which 4 g of N-chloro-succinimide dissolved in 20 ml of dimethylformamide was added dropwise at room temperature and the mixture was stirred overnight. The reaction mixture was poured into 100 ml of water, which was extracted with n-hexane. The organic layer was washed with a saturated brine, dried over anhydrous sodium sulfate and the solvent was evaporated under reduced pressure. Using the resultant crude 4-s-butyl-2-chloroaniline in the same way as that described in Example 1,4-hydroxy-6-s-butyl-8-chloro-2,3-dimethylquinoline was obtained. Using it as a starting material, 287.5 mg of 4-acetoxy-6-s-butyl-8-chloro-2,3-dimethylquinoline was obtained in the same way as that described in Example 10 (yield 17%). Its NMR spectral data are shown in the following Table 2.

Examples 25 and 26

The following compounds were synthesized in the same way as that described in Example 23. NMR spectral data of the thus-obtained compounds are shown in the following Table 2.

Example 25

Compound No. 216 (yield 31%)

Example 26

Compound No. 218 (yield 8%)

Example 27

Synthesis of 4-acetoxy-6-s-butyl-8-methoxy-2,3-dimethylqunoline (Compound No. 220)

4-s-Butyl-2-methoxyaniline was obtained using 3-methoxyacetophenone as a starting material according to various known reactions. Using 530 mg of the thus-obtained 4-s-butyl-2-methoxyaniline, 264 mg of 4-acetoxy-6-s-butyl-8-methoxy-2,3-dimethylquinoline was obtained in the same way as that described in Examples 1 and 10 (yield 40%). Its NMR spectral data are shown in the following Table 2.

Examples 28 to 32

The following compounds were synthesized in the same way as that described in Example 26. NMR spectral data of the thus-obtained compounds are shown in the following table 2.

Example 28

Compound No. 262 (yield 53%)

Example 29

Compound No. 268 (yield 42%)

Example 30

Compound No. 274 (yield 49%)

Example 31

Compound No. 280 (yield 39%)

Example 32

Compound No. 348 (yield 40%)

Example 33

Synthesis of 4-acetoxy-6-s-butyl-8-formyl-2,3-dimethylquinoline (Compound No. 356)

Grams of 4-hydroxy-6-s-butyl-8-bromo-2,3-dimethylquinoline synthesized in the same way as that described in Example 1 was suspended in 20 ml of dimethylformamide, to which 700 mg of 60% sodium hydride was added under cooling with ice and the mixture was stirred at room temperature for 30 minutes. To the reaction mixture was added dropwise 3 g of benzyl bromide under cooling with ice and the mixture was allowed to react at room temperature overnight. After the addition of 50 ml of water, the reaction mixture was extracted with ethyl acetate. The organic layer was washed with a saturated brine and dried over anhydrous sodium sulfate overnight. After the solvent was evaporated under reduced pressure, the resultant crude product was purified by column chromatography on silica gel (WAKOGEL® C-200) eluting with n-hexane to obtain 2.5 g of 4-benzyloxy-6-s-butyl-8-bromo-2,3-dimethylquinoline. 2.5 Grams of the thus-obtained 4-benzyloxy-6-s-butyl-8-bromo-2,3-dimethylquinoline was dissolved in 25 ml of anhydrous tetrahydrofuran and cooled to −78° C., to which 2.8 ml of a 2.5 M solution of n-butyl lithium in n-hexane was added dropwise and the mixture was stirred for 10 minutes. One ml of methyl formate dissolved in 2 ml of anhydrous tetrahydrofuran was added dropwise to the reaction mixture and the mixture was stirred at 0° C. for 30 minutes. After the addition of 50 ml of water, the reaction mixture was extracted with ethyl acetate. The organic layer was washed with an aqueous saturated ammonium chloride solution and a saturated brine and then dried over anhydrous sodium sulfate. After the solvent was evaporated under reduced pressure, the residue was purified by column chromatography on silica gel (WAKOGEL® C-200) eluting with n-hexane/ethyl acetate (20:1) to Obtain 800 mg of 4-benzyloxy-6-s-butyl-8-formyl-2,3-dimethylquinoline.

800 Milligrams of the resultant 4-benzyloxy-6-s-butyl-8-formyl-2,3-dimethylquinoline was dissolved in 2.5 ml of 20% sulfuric acid and stirred at 100° C. for 1 hour. After cooling to room temperature, the reaction mixture was neutralized with an aqueous saturated sodium hydrogencarbonate solution to produce precipitates, which were washed with water and n-hexane and then dried under reduced pressure to obtain 490 mg of 4-hydroxy-6-s-butyl-8-formyl-2,3-dimethylquinoline. 440 Milligrams of 4-hydroxy-6-s-butyl-8-formyl-2,3-dimethylquinoline was suspended in a mixture of 3 ml of acetic anhydride and 0.5 ml of pyridine and the mixture was stirred at 120° C. for 1.5 hours. The reaction mixture was cooled to room temperature, neutralized with an aqueous saturated sodium hydrogencarbonate solution and extracted with ethyl acetate. The resultant organic layer was washed with a saturated brine and dried over anhydrous sodium sulfate. After the solvent was evaporated, the resultant crude product was purified by column chromatography on silica gel (WAKOGEL® C-200) eluting with n-hexane/ethyl acetate (10:1) to obtain 220 mg of 4-acetoxy-6-s-butyl-8-formyl-2,3-dimethylquinoline (yield 13%). Its NMR spectral data are shown in the following Table 2.

Example 34

Synthesis of 4-acetoxy-6-s-butyl-8-hydroxymethyl-2,3-dimethylquinoline (Compound No. 340)

210 Milligrams of 4-acetoxy-6-s-butyl-8-formyl-2,3-dimethylquinoline obtained in Example 33 was dissolved in 4 ml of methanol, to which 7 mg of sodium borohydride dissolved in 4 ml of methanol was added dropwise and the mixture was stirred at room temperature for 1 minute. After the addition of 20 ml of water, the reaction mixture was extracted with ethyl acetate. The resultant organic layer was washed with a saturated brine and dried over anhydrous sodium sulfate. After the solvent was evaporated under reduced pressure, the resultant crude product was purified by column chromatography on silica gel (WAKOGEL® C-200) eluting with n-hexane/ethyl acetate (10:1) to obtain 186 mg of 4-acetoxy-6-s-butyl-8-hydroxymethyl-2,3-dimethylquinoline (yield 84%). Its NMR spectral data are shown in the following Table 2.

Example 35

Synthesis of 4-acetoxy-6-s-butyl-8-chloromethyl-2,3-dimethylquinoline (Compound No. 344)

50 Milligrams of 4-acetoxy-6-s-butyl-8-hydroxymethyl-2,3-dimethylquinoline obtained in Example 34 was dissolved in 0.3 ml of thionyl chloride and stirred at room temperature for 4.5 hours. After thionyl chloride was evaporated under reduced pressure, 0.5 ml of acetic anhydride was added to the resultant crude product and the mixture was stirred at 120° C. for 2 hours. After acetic anhydride was evaporated under reduced pressure, the resultant residue was purified by column chromatography on silica gel (WAKOGEL® C-200) eluting with n-hexane/ethyl acetate (20:1) to obtain 12.5 mg of 4-acetoxy-6-s-butyl-8-chloromethyl-2,3-dimethylquinoline (yield 23.5%). Its NMR spectral data are shown in the following Table 2.

TABLE 2

| compound No. | NMR spectral data |
|---|---|
| 97 | 11.37(1H, s), 7.83(1H, s), 7.42(1H, dd, $J_1$=8.6, $J_2$=1.6), 7.39(1H, d, J=8.6), 2.65(2H, t, J=7.4), 2.36(3H, s), 1.96(3H, s), 1.59(2H, m), 1.29(4H, m), 0.85(3H, t, J=6.8) solvent: DMSO-$d_6$ |
| 98 | 7.94(1H, d, J=8.7), 7.49(1H, dd, $J_1$=8.7, $J_2$=1.7), 7.42(1H, s), 2.75(2H, m), 2.71(3H, s), 2.52(3H, s), 2.25(3H, s), 1.68(2H, m), 1.34(4H, m), 0.90(3H, t, J=6.7) solvent: $CDCl_3$ |
| 107 | 11.36(1H, s), 7.83(1H, br.s), 7.39(2H, m), 2.65(2H, m), 2.35(3H, s), 1.95(3H, s), 1.58(2H, m), 1.27(6H, m), 0.85(3H, t, J=6.9) solvent: DMSO-$d_6$ |
| 108 | 7.92(1H, d, J=8.6), 7.49(1H, d, J=8.6), 7.42(1H, s), 2.75(2H, t, J=7.8), 2.71(3H, s), 2.52(3H, s), 2.24(3H, s), 1.67(2H, m), 1.39~1.28(6H, m), 0.88(3H, t, J=7.6) solvent: $CDCl_3$ |
| 111 | 11.32(1H, s), 7.85(1H, d, J=2.0), 7.44(1H, dd, $J_1$=8.5, $J_2$=2.2), 7.38(1H, d, J=8.6), 2.60(1H, m), 2.34(3H, s), 1.95(3H, s), 1.81(4H, m), 1.70(1H, m), 1.39(4H, m), 1.25(1H, m) solvent: DMSO-$d_6$ |
| 112 | 8.18(1H, d, J=2.0), 7.93(1H, d, J=8.8), 7.53(1H, dd, $J_1$=8.8, $J_2$=2.0), 2.86(3H, s), 2.72(1H, m), 2.70(3H, s), 2.52(3H, s), 1.80(4H, m), 1.77(1H, m), 1.46(4H, m), 1.31(1H, m) solvent: $CDCl_3$ |
| 125 | 11.35(1H, s), 7.83(1H, br.s), 7.40(2H, m), 2.65(2H, m), 2.35(3H, s), 1.95(3H, s), 1.58(2H, m), 1.27~1.23(10H, m), 0.84(3H, t, J=6.6) solvent: DMSO-$d_6$ |
| 126 | 7.93(1H, d, J=8.8), 7.49(1H, dd, $J_1$=8.8, $J_2$=1.9), 7.42(1H, d, J=1.2), 2.75(2H, t, J=7.8), 2.71(3H, s), 2.52(3H, s), 2.24(3H, s), 1.71~1.25(10H, m), 0.87(3H, t, J=6.9) solvent: $CDCl_3$ |
| 131 | 11.78(1H, s), 8.33(1H, br.s), 7.86(1H, dd, $J_1$=8.8, $J_2$=2.0), 7.66(1H, d, J=8.8), 2.40(3H, s), 1.98(3H, s) solvent: DMSO-$d_6$ |
| 132 | 8.12(1H, d, J=9.0), 8.00(1H, br.s), 7.82(1H, dd, $J_1$=9.0, $J_2$=2.0), 2.54(3H, s), 2.30(3H, s), 2.28(3H, s) solvent: $CDCl_3$ |
| 135 | 11.53(1H, s), 7.54(1H, d, J=9.0), 7.47(1H, d, J=3.1), 7.41(2H, dd, $J_1$=8.6, $J_2$=7.5), 7.37(2H, dd, $J_1$=9.0, $J_2$=3.1), 7.16(1H, t, J=7.5), 7.04(2H, dd, $J_1$=8.6, $J_2$=1.0), 2.37(3H, s), 1.94(3H, s) solvent: DMSO-$d_6$ |
| 136 | 7.98(1H, d, J=9.4), 7.38(2H, br.d, J=8.6), 7.35(1H, d, J=2.7), 7.18(1H, d, J=2.7), 7.14(1H, br.d, J=6.7), 7.06(2H, br.dd, $J_1$=8.6, $J_2$=0.8), 2.71(3H, s), 2.40(3H, s) solvent: $CDCl_3$ |
| 152 | 11.83(1H, s), 7.90(1H, s), 7.43(2H, s), 2.97(1H, t), 2.68(3H, m), 2.04(2H, t), 1.60(2H, t), 1.23(3H, d), 0.77(3H, t) solvent: DMSO-$d_6$ |
| 153 | 7.97(1H, d, J=8.8), 7.54(1H, d, J=1.9), 7.51(1H, dd, $J_1$=8.8, $J_2$=1.9), 3.19(2H, t, J=7.7), 2.95(2H, t, J=7.4), 2.76(1H, m), 2.49(3H, s), 2.20(2H, quint, J=7.4), 1.67(2H, quint, J=7.4), 1.31(3H, d, J=6.9), 0.84(3H, t, J=7.3) solvent: $CDCl_3$ |
| 154 | 11.20(1H, s), 7.36(1H, d, J=8.7), 7.21(1H, d, J=2.0), 7.10(1H, dd, $J_1$=8.7, $J_2$=2.0), 3.38(4H, q, J=6.9), 2.34(3H, s), 1.97(3H, s), 1.11(6H, t, J=6.9) solvent: DMSO-$d_6$ |
| 155 | 8.56(1H, d, J=2.8), 7.85(1H, d, J=9.3), 7.20(1H, dd, $J_1$=9.3, $J_2$=2.8), 3.44(4H, q, J=7.0), 2.64(3H, s), 2.48(3H, s), 2.21(3H, s), 1.21(6H, t, J=7.0) solvent: $CDCl_3$ |
| 156 | 11.23(1H, s), 7.40(3H, m), 3.86(4H, m), 3.11(4H, m), 2.35(3H, s), 2.06(3H, s) solvent: DMSO-$d_6$ |
| 157 | 8.85(1H, d, J=2.7), 7.90(1H, d, J=9.2), 7.39(1H, dd, $J_1$=9.2, $J_2$=2.7), 3.90(4H, m), 3.26(4H, m), 2.67(3H, s), 2.50(3H, s), 2.23(3H, s) solvent: $CDCl_3$ |
| 206 | 7.31(1H, s), 7.24(1H, s), 2.74(3H, s), 2.69(2H, s), 2.67(1H, m) 2.48(3H, s), 2.21(3H, s), 1.63(2H, m), 1.27(3H, d, J=7.0) 0.81(3H, t, J=7.0) solvent: $CDCl_3$ |
| 212 | 7.21(1H, m), 7.19(1H, m), 2.74(1H, m), 2.73(3H, s), 2.50(3H, s) 2.24(3H, s), 1.62(2H, m), 1.27(3H, d, J=7.0), 0.82(3H, t, J=7.0) solvent: $CDCl_3$ |
| 214 | 7.63(1H, d, J=2.0), 7.34(1H, d, J=2.0), 2.77(3H, s), 2.73(1H, m), 2.51(3H, s), 2.25(3H, s), 1.65(2H, m), 1.30(3H, d, J=6.9), 0.84(3H, t, J=7.3) solvent: $CDCl_3$ |
| 216 | 7.62(1H, d, J=1.9), 7.35(1H, d, J=1.7), 2.77(3H, s), 2.73(2H, t, J=7.8) 2.51(3H, s), 2.25(3H, s), 1.66(2H, m), 1.39(2H, m), 0.95(3H, t, J=7.3) solvent: $CDCl_3$ |

TABLE 2-continued

| compound No. | NMR spectral data |
|---|---|
| 218 | 7.83(1H, d, J=2.0), 7.51(1H, d, J=1.9), 2.77(3H, s), 2.51(3H, s) 2.25(3H, s), 1.39(9H, s) solvent: CDCl$_3$ |
| 220 | 7.01(1H, d, J=1.5), 6.84(1H, d, J=1.5), 4.06(3H, s), 2.75(3H, s) 2.71(1H, m), 2.50(3H, s), 2.24(3H, s), 1.66(2H, m), 1.30(3H, d, J=6.8), 0.85(3H, t, J=7.5) solvent: CDCl$_3$ |
| 262 | 7.31(1H, s), 7.27(1H, s), 2.74(3H, s), 2.70(3H, s), 2.50(3H, s), 2.46(3H, s), 2.23(3H, s) solvent: CDCl$_3$ |
| 268 | 7.34(1H, s), 7.28(1H, s), 3.25(2H, q, J=7.5), 2.77(2H, q, J=7.5) 2.70(3H, s), 2.23(3H, s), 1.35(3H, t, J=7.5), 1.30(3H, t, J=7.6) solvent: CDCl$_3$ |
| 274 | 7.40(1H, d, J=2.0), 7.28(1H, d, J=1.9), 4.31(1H, m), 3.04(1H, m) 2.69(3H, s), 2.50(3H, s), 2.23(3H, s), 1.36(6H, d, J=6.8), 1.31(6H, d, J=7.0) solvent: CDCl$_3$ |
| 280 | 7.30(1H, d, J=1.7), 7.24(1H, d, J=1.7), 4.13(1H, m), 2.73(1H, m), 2.69(3H, s), 2.51(3H, s), 2.22(3H, s), 1.61~1.84(4H, m) 1.31(3H, d, J=7.0), 1.30(3H, d, J=7.3), 0.87(3H, t, J=7.3), 0.83(3H, t, J=7.0) solvent: CDCl$_3$ |
| 334 | 7.90(1H, d J=8.5), 7.44(1H, dd J1 =8.5, J2 =2.0), 7.37(1H, d J=2.0), 2.71(3H, s), 2.65(2H, s), 2.51(3H, s), 2.56(3H, s), 0.93(9H, s) solvent: CDCl$_3$ |
| 338 | 7.58(1H, d J=1.7), 7.31(1H, d J=1.7), 2.78(3H, s), 2.63(2H, s), 2.51(3H, s), 2.27(3H, s), 0.95(9H, s) solvent: CDCl$_3$ |
| 340 | 7.34(1H, d, J=1.7), 7.33(1H, d, J=1.7), 5.64(1H, br.s), 5.12(2H, s) 2.75(1H, m), 2.70(3H, m), 2.51(3H, s), 2.25(3H, s), 1.65(2H, m) 1.29(3H, d, J=6.8), 0.83(3H, t, J=7.3) solvent: CDCl$_3$ |
| 344 | 7.64(1H, d, J=2.0), 7.39(1H, d, J=1.9), 5.32(2H, s), 2.75(1H, m), 2.71(3H, s), 2.51(3H, s), 2.24(3H, s), 1.66(2H, m), 1.31(3H, d =, J=6.8), 0.84(3H, t, J=7.3) solvent: CDCl$_3$ |
| 348 | 7.33(1H, d, J=2.0), 7.25(1H, d, J=2.0), 3.25(2H, q, J=7.4), 2.73(1H, m), 2.70(3H, s), 2.50(3H, s), 2.23(3H, s), 1.65(2H, m), 1.36(3H, t, J=7.6), 1.29(3H, d, J=7.0), 0.84(3H, t, J=7.4) solvent: CDCl$_3$ |
| 352 | 7.37(1H, s), 7.29(1H, s), 3.08(1H, m), 2.73(3H, s), 2.69(3H, s), 2.48(3H, s), 2.09(3H, s), 1.7~2.2(8H, m) solvent: CDCl$_3$ |
| 356 | 11.43(1H, s), 8.12(1H, d, J=2.2), 7.69(1H, d, J=2.0), 2.82(1H, m), 2.76(3H, s), 2.54(3H, s), 2.28(3H, s), 1.69(2H, m), 1.32(3H, d, J=6.8), 0.83(3H, t, J=7.3) solvent: CDCl$_3$ |
| 360 | 7.53(1H, s), 7.40(1H, s), 5.95(1H, m), 2.74(3H, s), 2.69(3H, s), 2.50 (3H, s), 2.22(3H, s), 2.07(3H, s), 1.82(3H, d, J=6.8) solvent: CDCl$_3$ |
| 362 | 7.39–7.47(2H, m), 5.98(1H, m), 2.73(3H, s), 2.49(3H, s), 2.24 (3H, s), 2.06(3H, s), 1.83(3H, d, J=7.1) solvent: CDCl$_3$ |

In the above tables, s, d, t, q, quint and m mean singlet, doublet, triplet, quartet, quintet and multiplet, respectively. And, DCDl$_3$ and DMSO-d$_6$ mean deuterium chloroform and deuterium DMSO, respectively.

Formulation Example 1 (Wettable Powder)

The following ingredients:

| | |
|---|---|
| the present compound (Compound No. 29) | 25% by weight |
| clay | 30% by weight |
| diatomaceous earth | 35% by weight |
| calcium lignin sulfonate | 3% by weight |
| polyoxyethylene alkyl aryl ether | 7% by weight |
| were uniformly mixed and pulverized to obtain a wettable powder. | |

Formulation Example 2 (Dust Formulation)

The following ingredients:

| | |
|---|---|
| the present compound (Compound No. 29) | 2% by weight |
| clay | 60% by weight |
| talc | 37% by weight |
| calcium stearate | 1% by weight |
| were uniformly mixed to obtain a dust formulation. | |

Formulation Example 3 (Emulsifiable Concentrate)

The following ingredients:

| | |
|---|---|
| the present compound (Compound No. 29) | 20% by weight |
| N,N-dimethylformamide | 20% by weight |
| xylene | 50% by weight |
| polyoxyethylene alkyl aryl ether | 10% by weight |
| were added, uniformly mixed and dissolved to obtain an emulsifiable concentrate. | |

Formulation Example 4 (Granule)

The following ingredients:

| | |
|---|---|
| the present compound (Compound No. 29) | 5% by weight |
| bentonite | 40% by weight |
| talc | 53% by weight |
| calcium lignin sulfonate | 2% by weight |
| were uniformly mixed with grinding, to which water was added, well kneaded, granulated and then dried to obtain a granule. | |

Test Example 1 (Test for Control Effect Against Rice Blast)

A spray liquid comprising a test compound whose concentration was adjusted to be 100 ppm by dilution with water was sprayed to a rice seedling (variety: Jikkoku) of 4-leaf stage grown id a vinyl pot of 5 cm in diameter by means of a spray gun. The air-dried rice seedling was inoculated with a conidium suspension of *Pyricularia oryzae* on the day of said application. For 40 hours after the inoculation, the rice seeding was under moist condition to complete infection with *Pyricularia oryzae* and then grown in an air-conditioned greenhouse. 6 Days after the inoculation, the lesion number on the fourth-leaf was counted. The protective value was calculated by comparing the lesion number in a treated area with that in an untreated area. Then, control effect was ranked according to the following criterion.

A; protective value ≧80%
B; protective value 50 to 79%
C; protective value <50%

Results are shown in Table 3.

TABLE 3

| compound No. | rank |
|---|---|
| 2 | B |
| 9 | A |
| 10 | A |
| 13 | A |
| 14 | A |
| 23 | B |
| 24 | B |
| 28 | A |
| 29 | A |
| 31 | A |
| 44 | A |
| 45 | A |
| 46 | A |
| 47 | A |
| 48 | A |
| 49 | A |
| 54 | A |
| 55 | A |
| 56 | A |
| 57 | A |
| 61 | A |
| 62 | A |
| 63 | A |
| 65 | A |
| 66 | A |
| 67 | A |
| 68 | A |
| 69 | A |
| 70 | A |
| 72 | B |
| 83 | A |
| 84 | A |
| 92 | B |
| 93 | A |
| 97 | B |
| 98 | A |
| 107 | A |
| 108 | A |
| 111 | B |
| 112 | A |
| 125 | B |
| 126 | A |
| 131 | B |
| 136 | A |
| 153 | B |
| 170 | A |
| 171 | B |
| 172 | A |
| 173 | A |
| 179 | A |
| 180 | A |
| 182 | B |
| 183 | B |
| 185 | B |
| 186 | B |
| 190 | B |
| 191 | A |
| 192 | A |
| 193 | A |
| 195 | A |
| 197 | A |
| 198 | B |
| 199 | A |
| 200 | A |
| 206 | A |
| 212 | A |
| 214 | A |
| 216 | A |
| 218 | A |
| 220 | A |
| 262 | B |
| 268 | A |
| 274 | A |
| 340 | A |
| 344 | A |
| 348 | A |
| 352 | A |
| 356 | A |
| 360 | A |
| 362 | A |

Test Example 2 (Test for Control Effect Against Powdery Mildew) of *Cucurbitaceae*)

A spray liquid comprising a test compound whose concentration was adjusted to be 200 ppm by dilution with water was sprayed to a cucumber grown in a vinyl pot of 3 cm in diameter when its first foliage leaf was developed. The air-dried cucumber seedling was inoculated with a conidium suspension of *Sphaerotheca fuliginea*. Thereafter, the cucumber seedling was transferred in an air-conditioned greenhouse. 10 Days after the inoculation, the disease severity was observed. The protective value was calculated by comparing the disease severity in a treated area with that in an untreated area. Then, control effect was ranked according to the following criterion.

A; protective value ≧80%
B; protective value 50 to 79%
C; protective value <50%

Results are shown in Table 4.

TABLE 4

| compound No. | rank |
|---|---|
| 24 | A |
| 29 | B |
| 45 | B |
| 55 | A |
| 56 | A |
| 61 | B |
| 65 | A |
| 66 | A |
| 67 | A |
| 68 | A |
| 71 | A |

TABLE 4-continued

| compound No. | rank |
|---|---|
| 72 | A |
| 93 | A |
| 112 | A |
| 136 | A |
| 153 | A |
| 175 | A |
| 176 | A |
| 185 | A |
| 195 | A |
| 196 | A |
| 197 | A |
| 214 | A |
| 216 | B |
| 218 | A |
| 268 | B |
| 340 | A |
| 344 | A |
| 348 | A |
| 356 | A |

Test Example 3 (Test for Antifungal Activity)

A test compound dissolved in acetone was mixed in a potato dextrose agar medium (manufactured by Nissui Seiyaku K.K.) so that the final concentration of the test compound was 100 ppm and then poured in a Petri dish. To this Perti dish after the agar was completely solidified, a cylindrical section prepared by punching a mycelial colony of each of plant pathogenic fungi cultured in another Petri dish by means of a cork borer was inoculated and cultured at 28 or 22° C. 48 Hours after the inoculation, the diameter of the mycelial colony was determined. Control percentages were calculated by comparing the diameter of the mycelial colony in a treated area with that in an untreated area. And, antifungal effect was ranked according to the following criterion.

A; control percentage ≧80%
B; control percentage 50 to 79%
C; control percentage <50%
Results are shown in Table 5.

TABLE 5

| Plant pathogen | Compoud No. | | | |
|---|---|---|---|---|
| | 10 | 28 | 29 | 31 |
| *Pyricularia oryzae* | A | B | A | A |
| *Rhizoctonia solani* | C | C | C | C |
| *Cochioborus miyabeanus* | B | C | B | A |
| *Gibberella fujikuroi* | C | C | B | A |
| *Botrytis cinerea* | C | C | B | A |
| *Fusarium oxysporum* f. sp. *lycopersici* | C | C | B | A |
| *Glomerella cingalata* | B | B | A | A |
| *Sclerotinia minor* | C | C | C | B |
| *Colletotrichum atramentarium* | B | B | B | A |
| *Alternaria alternata* Japanese pear pathotype | C | C | C | A |
| *Verticillium aibo-atrum* | C | A | A | A |

EFFECT OF THE INVENTION

The new 4-quinolinol derivatives represented by the general formula (I) of the present invention have an effective action as an agricultural and horticultural fungicide.eb; normal

The invention claimed is:

1. A 4-quinolinol compound represented by the formula (I):

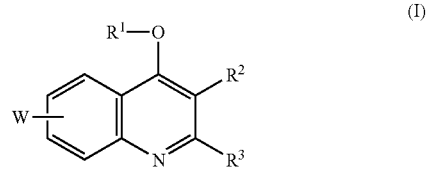

or an agricultural and horticulturally acceptable acid addition salt thereof, wherein $R^1$ represents
an alkali metal,
an alkaline earth metal, or
$COR^4$ in which $R^4$ is
  a hydrogen atom,
  an optionally substituted C1–C18 alkyl group,
  an optionally substituted C2–C18 alkenyl group,
  an optionally substituted C3–C10 cycloalkyl group,
  an optionally substituted phenyl C1–C4 alkyl group,
  an optionally substituted phenoxy C1–C4 alkyl group,
  an optionally substituted aryl group,
$OR^5$ in which $R^5$ is an optionally substituted C1–C4 alkyl group, an optionally substituted aryl group, an optionally substituted heterocycle, an optionally substituted phenyl C1–C4 alkyl group or an optionally substituted phenoxy C1–C4 alkyl group, or
$NR^6R^7$ in which $R^6$ and $R^7$ are each a hydrogen atom, an optionally substituted C1–C6 alkyl group or an optionally substituted phenyl group, or $R^1$ and $R^7$ together with N may form a four- to six-membered ring containing one or two heteroatoms;
$R^2$ represents an optionally substituted C1–C4 alkyl group;
$R^3$ represents an optionally substituted C1–C18 alkyl group; and
W represents 1 to 4 substituents on the nucleus which may be identical or different and each of which is
an optionally substituted C2–C4 alkenyl group,
an optionally substituted C2–C4 alkynyl group,
an optionally substituted C3–C10 cycloalkyl group,
an optionally substituted aryl group,
an optionally substituted aryloxy group,
$NR^8R^9$ in which $R^8$ and $R^9$ are each a hydrogen atom, an optionally substituted C1–C6 alkyl group or an optionally substituted phenyl group, or $R^1$ and $R^9$ together with N may form a four- to six-membered ring containing one or two heteroatoms,
$COR^{10}$ in which $R^{10}$ is a hydrogen atom, an optionally substituted C1–C4 alkyl group or an optionally substituted C2–C4 alkenyl group,
$COOR^{11}$ in which $R^{11}$ is a hydrogen atom, an optionally substituted C1–C4 alkyl group or an optionally substituted C2–C4 alkenyl group,
a nitro group, or
a cyano group;
wherein when optionally substituents present, the optional group is selected from the group consisting of halogen, C1–C4 alkyl group, C1–C4 alkoxy group and hydroxyl.

2. A 4-quinolinol compound represented by the formula (I):

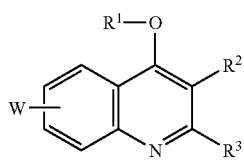

or an agricultural and horticulturally acceptable acid addition salt thereof, wherein $R^1$ represents
an alkali metal,
an alkaline earth metal, or
$COR^4$ in which $R^4$ is
  a hydrogen atom,
  an optionally substituted C1–C18 alkyl group,
  an optionally substituted C2–C18 alkenyl group,
  an optionally substituted C3–C10 cycloalkyl group,
  an optionally substituted phenyl C1–C4 alkyl group,
  an optionally substituted phenoxy C1–C4 alkyl group,
  an optionally substituted aryl group,
$OR^5$ in which $R^5$ is an optionally substituted C1–C4 alkyl group, an optionally substituted aryl group, an optionally substituted heterocycle, an optionally substituted phenyl C1–C4 alkyl group or an optionally substituted phenoxy C1–C4 alkyl group, or
$NR^6R^7$ in which $R^6$ and $R^7$ are each a hydrogen atom, an optionally substituted C1–C6 alkyl group or an optionally substituted phenyl group, or $R^6$ and $R^7$ together with N may form a four- to six-membered ring containing one or two heteroatoms;
$R^2$ represents an optionally substituted C1–C4 alkyl group;
$R^3$ represents an optionally substituted C2–C4 alkenyl group; and
W represents 1 to 4 substituents on the nucleus which may be identical or different and each of which is
an optionally substituted C2–C4 alkenyl group,
an optionally substituted C2–C4 alkynyl group,
an optionally substituted C3–C10 cycloalkyl group,
an optionally substituted aryl group,
an optionally substituted aryloxy group,
$NR^8R^9$ in which $R^8$ and $R^9$ are each a hydrogen atom, an optionally substituted C1–C6 alkyl group or an optionally substituted phenyl group, or $R^8$ and $R^9$ together with N may form a four- to six-membered ring containing one or two heteroatoms,
$COR^{10}$ in which $R^{10}$ is a hydrogen atom, an optionally substituted C1–C4 alkyl group or an optionally substituted C2–C4 alkenyl group,
$COOR^{11}$ in which $R^{11}$ is a hydrogen atom, an optionally substituted C1–C4 alkyl group or an optionally substituted C2–C4 alkenyl group,
a nitro group, or
a cyano group;
wherein when optionally substituents present, the optional group is selected from the group consisting of halogen, C1–C4 alkyl group, C1–C4 alkoxy group and hydroxyl.

3. A 4-quinolinol compound represented by the formula (I):

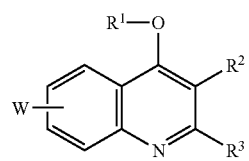

or an agricultural and horticulturally acceptable acid addition salt thereof, wherein $R^1$ represents
an alkali metal,
an alkaline earth metal, or
$COR^4$ in which $R^4$ is
  a hydrogen atom,
  an optionally substituted C1–C18 alkyl group,
  an optionally substituted C2–C18 alkenyl group,
  an optionally substituted C3–C10 cycloalkyl group,
  an optionally substituted phenyl C1–C4 alkyl group,
  an optionally substituted phenoxy C1–C4 alkyl group,
  an optionally substituted aryl group,
$OR^5$ in which $R^5$ is an optionally substituted C1–C4 alkyl group, an optionally substituted aryl group, an optionally substituted heterocycle, an optionally substituted phenyl C1–C4 alkyl group or an optionally substituted phenoxy C1–C4 alkyl group, or
$NR^6R^7$ in which $R^6$ and $R^7$ are each a hydrogen atom, an optionally substituted C1–C6 alkyl group or an optionally substituted phenyl group, or $R^6$ and $R^7$ together with N may form a four- to six-membered ring containing one or two heteroatoms;
$R^2$ represents an optionally substituted C1–C4 alkyl group;
$R^3$ represents an optionally substituted C1–C4 alkoxy group; and
W represents 1 to 4 substituents on the nucleus which may be identical or different and each of which is
a halogen atom,
an optionally substituted C1–C10 alkyl group,
an optionally substituted C2–C4 alkenyl group,
an optionally substituted C2–C4 alkynyl group,
an optionally substituted C1–C10 alkoxy group,
an optionally substituted C3–C10 cycloalkyl group,
an optionally substituted aryl group,
an optionally substituted aryloxy group,
$NR^8R^9$ in which $R^8$ and $R^9$ are each a hydrogen atom, an optionally substituted C1–C6 alkyl group or an optionally substituted phenyl group, or $R^8$ and $R^9$ together with N may form a four- to six-membered ring containing one or two heteroatoms,
$COR^{10}$ in which $R^{10}$ is a hydrogen atom, an optionally substituted C1–C4 alkyl group or an optionally substituted C2–C4 alkenyl group,
$COOR^{11}$ in which $R^{11}$ is a hydrogen atom, an optionally substituted C1–C4 alkyl group or an optionally substituted C2–C4 alkenyl group,
a nitro group, or
a cyano group;
wherein when optionally substituents present, the optional group is selected from the group consisting of halogen, C1–C4 alkyl, C1–C4 alkoxy group and hydroxyl.

4. A 4-quinolinol compound represented by the formula (I):

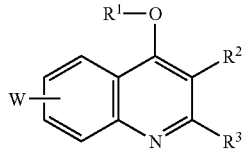

or an agricultural and horticulturally acceptable acid addition salt thereof, wherein $R^1$ represents
an alkali metal,
an alkaline earth metal, or
$COR^4$ in which $R^4$ is
  a hydrogen atom,
  an optionally substituted C1–C18 alkyl group,
  an optionally substituted C2–C18 alkenyl group,
  an optionally substituted C3–C10 cycloalkyl group,
  an optionally substituted phenyl C1–C4 alkyl group,
  an optionally substituted phenoxy C1–C4 alkyl group,
  an optionally substituted aryl group,
$OR^5$ in which $R^5$ is an optionally substituted C1–C4 alkyl group, an optionally substituted aryl group, an optionally substituted heterocycle, an optionally substituted phenyl C1–C4 alkyl group or an optionally substituted phenoxy C1–C4 alkyl group, or
$NR^6R^7$ in which $R^6$ and $R^7$ are each a hydrogen atom, an optionally substituted C1–C6 alkyl group or an optionally substituted phenyl group, or $R^6$ and $R^7$ together with N may form a four- to six-membered ring containing one or two heteroatoms;
$R^2$ and $R^3$ together represent —$(CH_2)m$- in which m is 3 or 4; and
W represents 1 to 4 substituents on the nucleus which may be identical or different and each of which is
an optionally substituted C2–C4 alkenyl group,
an optionally substituted C2–C4 alkynyl group,
an optionally substituted C3–C10 cycloalkyl group,
an optionally substituted aryl group,
an optionally substituted aryloxy group,
$NR^8R^9$ in which $R^8$ and $R^9$ are each a hydrogen atom, an optionally substituted C1–C6 alkyl group or an optionally substituted phenyl group, or $R^8$ and $R^9$ together with N may form a four- to six-membered ring containing one or two heteroatoms,
$COR^{10}$ in which $R^{10}$ is a hydrogen atom, an optionally substituted C1–C4 alkyl group or an optionally substituted C2–C4 alkenyl group,
$COOR^{11}$ in which $R^{11}$ is a hydrogen atom, an optionally substituted C1–C4 alkyl group or an optionally substituted C2–C4 alkenyl group,
a nitro group, or
a cyano group;
wherein when optionally substituents present, the optional group is selected from the group consisting of halogen, C1–C4 alkyl, C1–C4 alkoxy group and hydroxyl.

5. A 4-quinolinol compound represented by the formula (I):

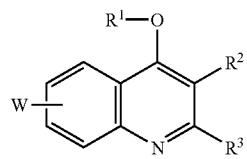

or an agricultural and horticulturally acceptable acid addition salt thereof, wherein $R^1$ represents a hydrogen atom;
$R^2$ represents an optionally substituted C1–C4 alkyl group;
$R^3$ represents an optionally substituted C1–C18 alkyl group; and
W represents 1 to 4 substituents on the nucleus which may be identical or different and each of which is
an optionally substituted C2–C4 alkenyl group,
an optionally substituted C2–C4 alkynyl group,
an optionally substituted C3–C10 cycloalkyl group,
an optionally substituted aryl group,
an optionally substituted aryloxy group,
$NR^8R^9$ in which $R^8$ and $R^9$ are each a hydrogen atom, an optionally substituted C1–C6 alkyl group or an optionally substituted phenyl group, or $R^8$ and $R^9$ together with N may form a four- to six-membered ring containing one or two heteroatoms,
$COR^{10}$ in which $R^{10}$ is a hydrogen atom, an optionally substituted C1–C4 alkyl group or an optionally substituted C2–C4 alkenyl group,
$COOR^{11}$ in which $R^{11}$ is a hydrogen atom, an optionally substituted C1–C4 alkyl group or an optionally substituted C2–C4 alkenyl group,
a nitro group, or
a cyano group;
wherein when optionally substituents present, the optional group is selected from the group consisting of halogen, C1–C4 alkyl group, C1–C4 alkoxy group and hydroxyl.

6. A 4-quinolinol compound represented by the formula (I):

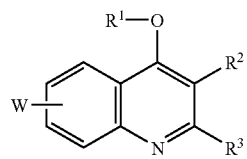

or an agricultural and horticulturally acceptable acid addition salt thereof, wherein $R^1$ represents a hydrogen atom;
$R^2$ represents an optionally substituted C1–C4 alkyl group;
$R^3$ represents an optionally substituted C2–C4 alkenyl group; and
W represents 1 substituents on the nucleus which may be
an optionally substituted C2–C4 alkenyl group,
an optionally substituted C2–C4 alkynyl group,
an optionally substituted C3–C10 cycloalkyl group,
an optionally substituted aryl group,
an optionally substituted aryloxy group, NR⁸R⁹ in which R⁸ and R⁹ are each a hydrogen atom, an optionally substituted C1–C6 alkyl group or an optionally substituted phenyl group, or R⁸ and R⁹ together with N may form a four- to six-membered ring containing one or two heteroatoms, COR¹⁰ in which R¹⁰ is a hydrogen atom, an optionally substituted C1–C4 alkyl group or an optionally substituted C2–C4 alkenyl group, COOR¹¹ in which R¹¹ is a hydrogen atom, an optionally substituted C1–C4 alkyl group or an optionally substituted C2–C4 alkenyl group, a nitro group, or a cyano group;

wherein when optionally substituents present, the optional group is selected from the group consisting of halogen, C1–C4 alkyl group, C1–C4 alkoxy group and hydroxyl.

7. A 4-quinolinol compound represented by the formula (I):

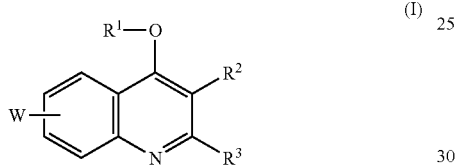

or an agricultural and horticulturally acceptable acid addition salt thereof, wherein R¹ represents a hydrogen atom;

R² represents an optionally substituted C1–C4 alkyl group;

R³ represents an optionally substituted C2–C4 alkenyl group; and

W represents 2 substituents on the nucleus which may be identical or different and each of which is an optionally substituted C2–C4 alkenyl group, an optionally substituted C2–C4 alkynyl group, an optionally substituted C3–C10 cycloalkyl group, an optionally substituted aryl group, an optionally substituted aryloxy group, NR⁸R⁹ in which R⁸ and R⁹ are each a hydrogen atom, an optionally substituted C1–C6 alkyl group or an optionally substituted phenyl group, or R⁸ and R⁹ together with N may form a four- to six-membered ring containing one or two heteroatoms, COR¹⁰ which R¹⁰ is a hydrogen atom, an optionally substituted C1–C4 alkyl group or an optionally substituted C2–C4 alkenyl group, COOR¹¹ in which R¹¹ is a hydrogen atom, an optionally substituted C1–C4 alkyl group or an optionally substituted C2–C4 alkenyl group, a nitro group, or a cyano group;

wherein when optionally substituents present, the optional group is selected from the group consisting of halogen, C1–C4 alkyl group, C1–C4 alkoxy group and hydroxyl.

8. A 4-quinolinol compound represented by the formula (I):

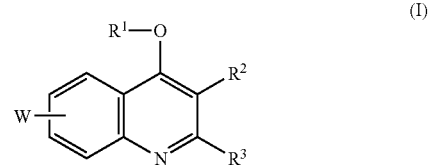

or an agricultural and horticulturally acceptable acid addition salt thereof, wherein R¹ represents a hydrogen atom;

R² represents an optionally substituted C1–C4 alkyl group;

R³ represents an optionally substituted C2–C4 alkenyl group; and

W represents 3 to 4 substituents on the nucleus which may be identical or different and each of which is an optionally substituted C2–C4 alkenyl group, an optionally substituted C2–C4 alkynyl group, an optionally substituted C3–C10 cycloalkyl group, an optionally substituted aryl group, an optionally substituted aryloxy group, NR⁸R⁹ in which R⁸ and R⁹ are each a hydrogen atom, an optionally substituted C1–C6 alkyl group or an optionally substituted phenyl group, or R⁸ and R⁹ together with N may form a four- to six-membered ring containing one or two heteroatoms, COR¹⁰ in which R¹⁰ is a hydrogen atom, an optionally substituted C1–C4 alkyl group or an optionally substituted C2–C4 alkenyl group, COOR¹¹ in which R¹¹ is a hydrogen atom, an optionally substituted C1–C4 alkyl group or an optionally substituted C2–C4 alkenyl group, a nitro group, or a cyano group;

wherein when optionally substituents present, the optional group is selected from the group consisting of halogen, C1–C4 alkyl group, C1–C4 alkoxy group and hydroxyl.

9. A 4-quinolinol compound represented by the formula (I):

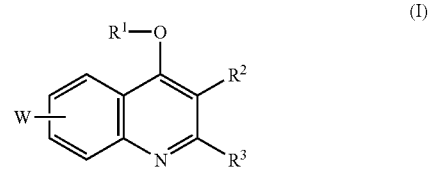

or an agricultural and horticulturally acceptable acid addition salt thereof, wherein R¹ represents a hydrogen atom;

R² represents an optionally substituted C1–C4 alkyl group;

R³ represents an optionally substituted C1–C4 alkoxy group; and

W represents 1 to 4 substituents on the nucleus which may be identical or different and each of which is a halogen atom, an optionally substituted C1–C10 alkyl group, an optionally substituted C2–C4 alkenyl group, an optionally substituted C2–C4 alkynyl group,
an optionally substituted C1–C10 alkoxy group,
an optionally substituted C3–C10 cycloalkyl group,
an optionally substituted aryl group,
an optionally substituted aryloxy group,
$NR^8R^9$ in which $R^8$ and $R^9$ are each a hydrogen atom, an optionally substituted C1–C6 alkyl group or an optionally substituted phenyl group, or $R^8$ and $R^9$ together with N may form a four- to six-membered ring containing one or two heteroatoms,
$COR^{10}$ in which $R^{10}$ is a hydrogen atom, an optionally substituted C1–C4 alkyl group or an optionally substituted C2–C4 alkenyl group,
$COOR^{11}$ in which $R^{11}$ is a hydrogen atom, an optionally substituted C1–C4 alkyl group or an optionally substituted C2–C4 alkenyl group,
a nitro group, or
a cyano group;
wherein when optionally substituents present, the optional group is selected from the group consisting of halogen, C1–C4 alkyl group, C1–C4 alkoxy group and hydroxyl.

10. A 4-quinolinol compound represented by the formula (I):

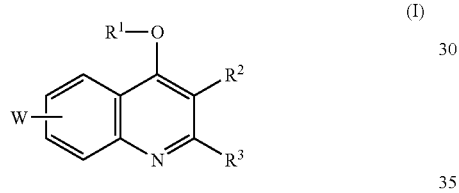

or an agricultural and horticulturally acceptable acid addition salt thereof, wherein $R^1$ represents a hydrogen atom;
$R^2$ and $R^3$ together represent —$(CH_2)m$- in which m is 3 or 4; and
W represents 1 substituent on the nucleus which is
a halogen atom,
an optionally substituted C2–C4 alkenyl group,
an optionally substituted C2–C4 alkynyl group,
an optionally substituted C1–C10 alkoxy group,
an optionally substituted aryl group,
an optionally substituted aryloxy group,
$NR^8R^9$ in which $R^8$ and $R^9$ are each a hydrogen atom, an optionally substituted C1–C6 alkyl group or an optionally substituted phenyl group, or $R^8$ and $R^9$ together with N may form a four- to six-membered ring containing one or two heteroatoms,
$COR^{10}$ in which $R^{10}$ is a hydrogen atom, an optionally substituted C1–C4 alkyl group or an optionally substituted C2–C4 alkenyl group,
$COOR^{11}$ in which $R^{11}$ is a hydrogen atom, an optionally substituted C1–C4 alkyl group or an optionally substituted C2–C4 alkenyl group,
a nitro group, or
a cyano group;
wherein when optionally substituents present, the optional group is selected from the group consisting of halogen, C1–C4 alkyl group, C1–C4 alkoxy group and hydroxyl.

11. A 4-quinolinol compound represented by the formula (I):

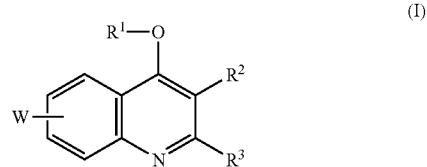

or an agricultural and horticulturally acceptable acid addition salt thereof wherein $R^1$ represents a hydrogen atom;
$R^2$ and $R^3$ together represent —$(CH_2)m$- in which m is 3 or 4; and
W represents 2 substituents on the nucleus which may be identical or different and each of which is
a halogen atom,
an optionally substituted C1–C10 alkyl group,
an optionally substituted C2–C4 alkenyl group,
an optionally substituted C2–C4 alkynyl group,
an optionally substituted C1–C10 alkoxy group,
an optionally substituted C3–C10 cycloalkyl group,
an optionally substituted aryl group,
an optionally substituted aryloxy group,
$NR^8R^9$ in which $R^8$ and $R^9$ are each a hydrogen atom, an optionally substituted C1–C6 alkyl group or an optionally substituted phenyl group, or $R^8$ and $R^9$ together with N may form a four- to six-membered ring containing one or two heteroatoms,
$COR^{10}$ in which $R^{10}$ is a hydrogen atom, an optionally substituted C1–C4 alkyl group or an optionally substituted C2–C4 alkenyl group,
$COOR^{11}$ in which $R^{11}$ is a hydrogen atom, an optionally substituted C1–C4 alkyl group or an optionally substituted C2–C4 alkenyl group,
a nitro group, or
a cyano group;
wherein when optionally substituents present, the optional group is selected from the group consisting of halogen, C1–C4 alkyl group, C1–C4 alkoxy group and hydroxyl.

12. A 4-quinolinol compound represented by the formula (I):

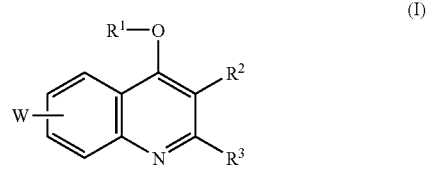

or an agricultural and horticulturally acceptable acid addition salt thereof, wherein $R^1$ represents a hydrogen atom;
$R^2$ and $R^3$ together represent —$(CH_2)m$- in which m is 3 or 4; and
W represents 3 to 4 substituents on the nucleus which may be identical or different and each of which is
a halogen atom,
an optionally substituted C1–C10 alkyl group,
an optionally substituted C2–C4 alkenyl group,
an optionally substituted C2–C4 alkynyl group, an optionally substituted C1–C10 alkoxy group,
an optionally substituted C3–C10 cycloalkyl group,
an optionally substituted aryl group,
an optionally substituted aryloxy group,
$NR^8R^9$ in which $R^8$ and $R^9$ are each a hydrogen atom, an optionally substituted C1–C6 alkyl group or an optionally substituted phenyl group, or $R^8$ and $R^9$ together with N may form a four- to six-membered ring containing one or two heteroatoms,
$COR^{10}$ in which $R^{10}$ is a hydrogen atom, an optionally substituted C1–C4 alkyl group or an optionally substituted C2–C4 alkenyl group,
$COOR^{11}$ in which $R^{11}$ is a hydrogen atom, an optionally substituted C1–C4 alkyl group or an optionally substituted C2–C4 alkenyl group,
a nitro group, or
a cyano group;
wherein when optionally substituents present, the optional group is selected from the group consisting of halogen, C1–C4 alkyl group, C1–C4 alkoxy group and hydroxyl.

13. A 4-quinolinol compound represented by the formula (I):

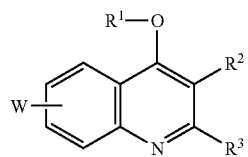

or an agricultural and horticulturally acceptable acid addition salt thereof, wherein $R^1$ is a hydrogen atom; $R^2$ and $R^3$ are each methyl; and W are 6-s-$C_4H_9$ and 8-$CH_2OH$.

14. A 4-quinolinol compound represented by the formula (I):

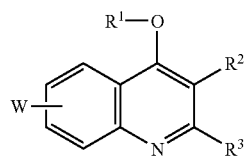

or an agricultural and horticulturally acceptable acid addition salt thereof, wherein $R^1$ is $CH_3CO$; $R^2$ and $R^3$ are each methyl; and W are 6-s-$C_4H_9$ and 8-$CH_2OH$.

15. A 4-quinolinol compound represented by the formula (I):

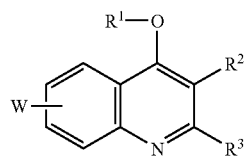

or an agricultural and horticulturally acceptable acid addition salt thereof, wherein $R^1$ is a hydrogen atom; $R^2$ and $R^3$ are each methyl; and W are 6-t-$C_4H_9$ and 8-$CH_2OH$.

16. A 4-quinolinol compound represented by the formula (I):

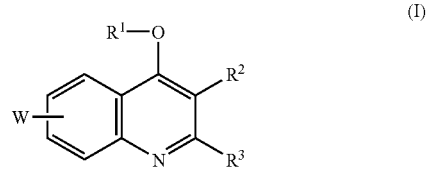

or an agricultural and horticulturally acceptable acid addition salt thereof, wherein $R^1$ is $CH_3CO$; $R^2$ and $R^3$ are each methyl; and W are 6-t-$C_4H_9$ and 8-$CH_2OH$.

17. A 4-quinolinol compound represented by the formula (I):

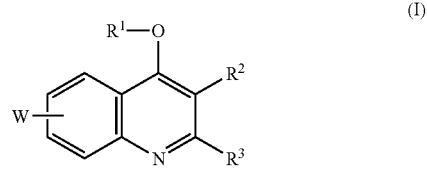

or an agricultural and horticulturally acceptable acid addition salt thereof, wherein $R^1$ is $CH_3CO$; $R^2$ and $R^3$ are each methyl; and W are 6-s-$C_4H_9$ and 8-$CH_2Cl$.

18. A 4-quinolinol compound represented by the formula (I):

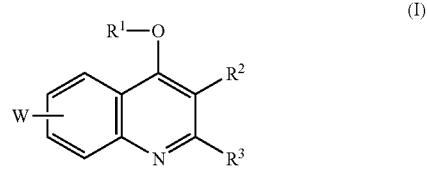

or an agricultural and horticulturally acceptable acid addition salt thereof, wherein $R^1$ is $CH_3CO$; $R^2$ and $R^3$ are each methyl; and W are 6-t-$C_4H_9$ and 8-$CH_2Cl$.

19. A 4-quinolinol compound represented by the formula (I):

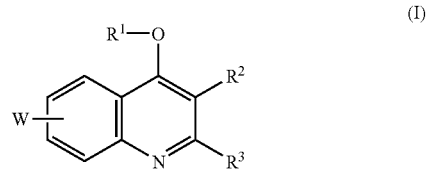

or an agricultural and horticulturally acceptable acid addition salt thereof, wherein $R^1$ is a hydrogen atom; $R^2$ and $R^3$ are each methyl; and W are 6-c-$C_5H_9$ and 8-methyl.

20. A 4-quinolinol compound represented by the formula (I):

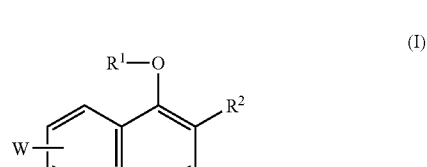

or an agricultural and horticulturally acceptable acid addition salt thereof, wherein R¹ is CH₃CO; R² and R³ are each methyl; and W are 6-c-C₅H₉ and 8-methyl.

21. A 4-quinolinol compound represented by the formula (I):

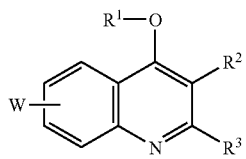

(I)

or an agricultural and horticulturally acceptable acid addition salt thereof, wherein R¹ is a hydrogen atom; R² and R³ are each methyl; and W are 6-c-C₅H₉ and 8-Cl.

22. A 4-quinolinol compound represented by the formula (I):

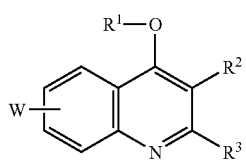

(I)

or an agricultural and horticulturally acceptable acid addition salt thereof, wherein R¹ is CH₃CO; R² and R³ are each methyl; and W are 6-c-C₅H₉ and 8-Cl.

23. A 4-quinolinol compound represented by the formula (I):

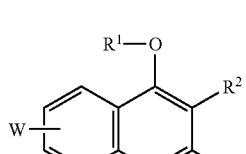

(I)

or an agricultural and horticulturally acceptable acid addition salt thereof, wherein R¹ is a hydrogen atom; R² and R³ are each methyl; and W are 6-s-C₄H₉ and 8-CHO.

24. A 4-quinolinol compound represented by the formula (I):

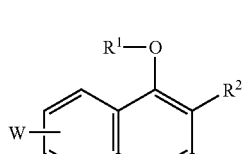

(I)

or an agricultural and horticulturally acceptable acid addition salt thereof, wherein R¹ is CH₃CO; R² and R³ are each methyl; and W are 6-s-C₄H₉ and 8-CHO.

25. A 4-quinolinol compound represented by the formula (I):

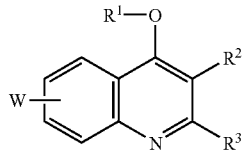

(I)

or an agricultural and horticulturally acceptable acid addition salt thereof wherein R¹ is a hydrogen atom; R² and R³ are each methyl; and W are 6-t-C₄H₉ and 8-CHO.

26. A 4-quinolinol compound represented by the formula (I):

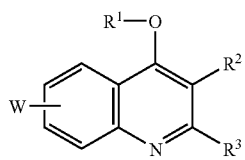

(I)

or an agricultural and horticulturally acceptable acid addition salt thereof, wherein R¹ is CH₃CO; R² and R³ are each methyl; and W are 6-t-C₄H₉ and 8-CHO.

27. A 4-quinolinol compound represented by the formula (I):

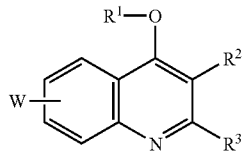

(I)

or an agricultural and horticulturally acceptable acid addition salt thereof, wherein R¹ is a hydrogen atom; R² and R³ are each methyl; and W are 6-CH₃CH=C(CH₃) and 8-methyl.

28. A 4-quinolinol compound represented by the formula (I):

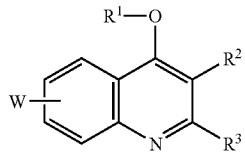

(I)

or an agricultural and horticulturally acceptable acid addition salt thereof, wherein R¹ is CH₃CO; R² and R³ are each methyl; and W are 6-CH₃CH=C(CH₃) and 8-methyl.

29. A 4-quinolinol compound represented by the formula (I):

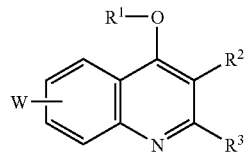

or an agricultural and horticulturally acceptable acid addition salt thereof, wherein $R^1$ is a hydrogen atom; $R^2$ and $R^3$ are each methyl; and W are 6-$CH_3CH=C(CH_3)$ and 8-F.

30. A 4-quinolinol compound represented by the formula (I):

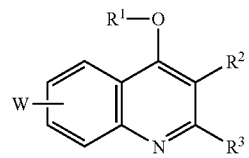

or an agricultural and horticulturally acceptable acid addition salt thereof, wherein $R^1$ is $CH_3CO$; $R^2$ and $R^3$ are each methyl; and W are 6-$CH_3CH=C(CH_3)$ and 8-F.

* * * * *